(12) United States Patent
Kuzumoto et al.

(10) Patent No.: US 11,069,863 B2
(45) Date of Patent: Jul. 20, 2021

(54) ORGANIC THIN FILM AND ORGANIC THIN FILM TRANSISTOR AND ELECTRONIC DEVICE

(71) Applicant: Samsung Electronics Co., Ltd., Suwon-si (KR)

(72) Inventors: Yasutaka Kuzumoto, Suwon-si (KR); Jeong Il Park, Seongnam-si (KR); Hyun Bum Kang, Yongin-si (KR); Eun Kyung Lee, Seoul (KR); Don-Wook Lee, Seoul (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 0 days.

(21) Appl. No.: 16/661,631

(22) Filed: Oct. 23, 2019

(65) Prior Publication Data
US 2020/0176690 A1   Jun. 4, 2020

(30) Foreign Application Priority Data

Dec. 3, 2018   (KR) .................. 10-2018-0153902

(51) Int. Cl.
| | | |
|---|---|---|
| H01L 51/00 | (2006.01) | |
| C07D 495/22 | (2006.01) | |
| H01L 51/10 | (2006.01) | |
| H01L 51/05 | (2006.01) | |

(52) U.S. Cl.
CPC ........ *H01L 51/0074* (2013.01); *C07D 495/22* (2013.01); *H01L 51/102* (2013.01); *H01L 51/0566* (2013.01)

(58) Field of Classification Search
CPC .......................... H01L 51/0074; C07D 495/22
See application file for complete search history.

(56) References Cited

U.S. PATENT DOCUMENTS

| | | |
|---|---|---|
| 8,124,964 B2 | 2/2012 | Takimiya et al. |
| 8,138,355 B2 | 3/2012 | Watanabe |
| 8,211,619 B2 | 7/2012 | Morita et al. |
| 8,232,546 B2 | 7/2012 | Takimiya et al. |
| 8,828,642 B2 | 9/2014 | Kamogawa et al. |
| 9,018,630 B2 | 4/2015 | Takimiya et al. |
| 9,096,621 B2 | 8/2015 | Hoffmann et al. |
| 9,373,795 B2 | 6/2016 | Burroughes et al. |
| 9,431,619 B2 | 8/2016 | Lee et al. |
| 9,537,102 B2 | 1/2017 | Park et al. |
| 9,853,225 B2 | 12/2017 | Takeya et al. |
| 9,988,472 B2 | 6/2018 | Lee et al. |
| 10,056,563 B2 | 8/2018 | Miyazaki et al. |
| 2008/0142792 A1 | 6/2008 | Park et al. |
| 2015/0133679 A1 | 5/2015 | Park et al. |
| 2016/0226005 A1 | 8/2016 | Park et al. |
| 2017/0069854 A1 | 3/2017 | Lee et al. |
| 2019/0036037 A1 | 1/2019 | Lee et al. |

FOREIGN PATENT DOCUMENTS

| | | |
|---|---|---|
| EP | 1932847 A1 | 6/2008 |
| EP | 3125321 A1 | 2/2017 |
| EP | 3301207 A1 | 4/2018 |
| EP | 3522243 A1 | 8/2019 |
| JP | 2007-122029 A | 5/2007 |
| JP | 2009267134 A | 11/2009 |
| JP | 2015-192116 A | 11/2015 |
| KR | 10-2014-0041439 A | 4/2014 |
| KR | 10-2014-0064965 A | 5/2014 |
| KR | 10-2019-0013429 A | 2/2019 |
| WO | WO-08026602 A1 | 3/2008 |
| WO | WO-2009-009790 A1 | 1/2009 |
| WO | WO-2012-118174 A1 | 9/2012 |
| WO | WO-14136827 A1 | 9/2014 |
| WO | WO-2016-117389 A1 | 7/2016 |
| WO | WO-2018-061821 A1 | 4/2018 |

OTHER PUBLICATIONS

STN search conducted Nov. 12, 2020 (Year: 2020).*
Nakayama, Kengo, et. al., "Patternable Solution-Crystallized Organic Transistors with High Charge Carrier Mobility" Advanced Materials, 2011, 23, 1626-1629.
He, Keqiang, et al., "Asymmetric Conjugated Molecules Based on [1]Benzothieno[3,2-b][1]benzothiophene for High-Mobility Organic Thin-Film Transistors: Influence of Alkyl Chain Length," ACS Applied Materials & Interfaces, Sep. 26, 2017.
Extended European Search Report dated May 7, 2020, issued in corresponding European Patent Application No. 19204586.2.

* cited by examiner

*Primary Examiner* — Noble E Jarrell
(74) *Attorney, Agent, or Firm* — Harness, Dickey & Pierce, P.L.C.

(57) ABSTRACT

Disclosed are an organic thin film includes a first compound represented by one of Chemical Formula 1A and 1B and a second compound different from the first compound and represented by one of Chemical Formulae 2A and 2B, an organic thin film transistor, and an electronic device.

30 Claims, 10 Drawing Sheets

ORGANIC THIN FILM AND ORGANIC THIN FILM TRANSISTOR AND ELECTRONIC DEVICE

CROSS-REFERENCE TO RELATED APPLICATION

This application claims priority to and the benefit of Korean Patent Application No. 10-2018-0153902 filed in the Korean Intellectual Property Office on Dec. 3, 2018, the entire contents of which are incorporated herein by reference.

BACKGROUND

1. Field

An organic thin film, an organic thin film transistor, and an electronic device are disclosed.

2. Description of Related Art

A flat panel display such as a liquid crystal display (LCD) or an organic light emitting diode (OLED) display includes a thin film transistor (TFT) that is a three-terminal element as a switch. Research on an organic thin film transistor (OTFT) including an organic semiconductor, such as a low molecular semiconductor or polymer semiconductor instead of an inorganic semiconductor such as a silicon (Si) semiconductor, as one kind of the thin film transistor are being actively conducted.

The organic thin film transistor may be made into a fiber or a film due to characteristics of an organic material, and thus is drawing attention as a core element for a flexible display device. The organic thin film transistor may be manufactured using a solution process such as inkjet printing, and may be easily applied to a large area flat panel display where a deposition process has a limit.

SUMMARY

An embodiment provides an organic thin film applicable to an electronic device such as an organic thin film transistor.

Another embodiment provides an organic thin film transistor including the organic thin film.

Yet another embodiment provides an electronic device including the organic thin film or the organic thin film transistor.

According to an embodiment, an organic thin film includes a first compound represented by one of Chemical Formula 1A and 1B and a second compound that is different from the first compound and represented by one of Chemical Formulae 2A and 2B.

[Chemical Formula 1A]

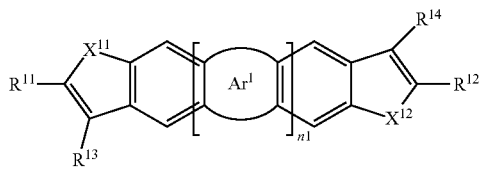

[Chemical Formula 1B]

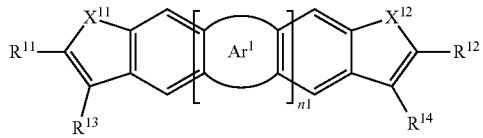

[Chemical Formula 2A]

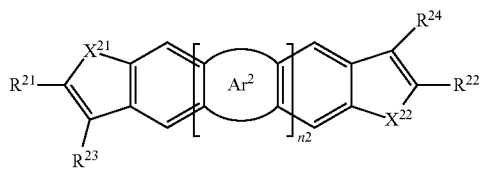

[Chemical Formula 2B]

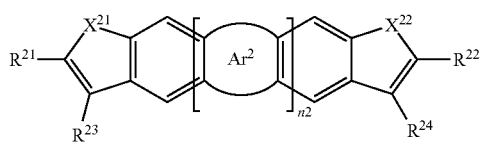

In Chemical Formulae 1A, 1B, 2A, and 2B, $X^{11}$, $X^{12}$, $X^{21}$, and $X^{22}$ are independently one of O, S, Se, Te, and $NR^a$, $Ar^1$ and $Ar^2$ independently include at least one substituted or unsubstituted benzene ring, at least one substituted or unsubstituted furan ring, at least one substituted or unsubstituted thiophene ring, at least one substituted or unsubstituted selenophene ring, at least one substituted or unsubstituted tellurophene ring, or a fused ring of two or more of the foregoing rings, $R^{11}$ and $R^{12}$ are different from each other and/or $R^{13}$ and $R^{14}$ are different from each other, $R^{21}$ and $R^{22}$ are different from each other and/or $R^{23}$ and $R^{24}$ are different from each other, $R^{11}$ to $R^{14}$, $R^{21}$ to $R^{24}$, and $R^a$ are independently hydrogen, a substituted or unsubstituted C1 to C30 alkyl group, a substituted or unsubstituted C2 to C30 alkenyl group, a substituted or unsubstituted C2 to C30 alkynyl group, a substituted or unsubstituted C3 to C30 cycloalkyl group, a substituted or unsubstituted C3 to C30 cycloalkenyl group, a substituted or unsubstituted C1 to C30 alkoxy group, a substituted or unsubstituted C3 to C30 heterocycloalkyl group, a substituted or unsubstituted C3 to C30 heterocycloalkenyl group, a substituted or unsubstituted C6 to C30 aryl group, a substituted or unsubstituted C7 to C30 alkylaryl group, a substituted or unsubstituted C6 to C30 aryloxy group, a substituted or unsubstituted C3 to C30 heteroaryl group, a substituted or unsubstituted C4 to C30 alkylheteroaryl group, a halogen, a cyano group, or a combination thereof, and n1 and n2 are independently 0 or 1.

In some embodiments, the organic thin film may include a mixture of the first compound and the second compound.

In some embodiments, $Ar^1$ and $Ar^2$ may independently include one to six rings and $Ar^1$ and $Ar^2$ may independently include at least one of a substituted or unsubstituted furan ring, a substituted or unsubstituted thiophene ring, a substituted or unsubstituted selenophene ring, and substituted or unsubstituted tellurophene ring.

In some embodiments, $Ar^1$ and $Ar^2$ may independently include a structure represented by a substituted or unsubstituted group listed in Group 1.

[Group 1]

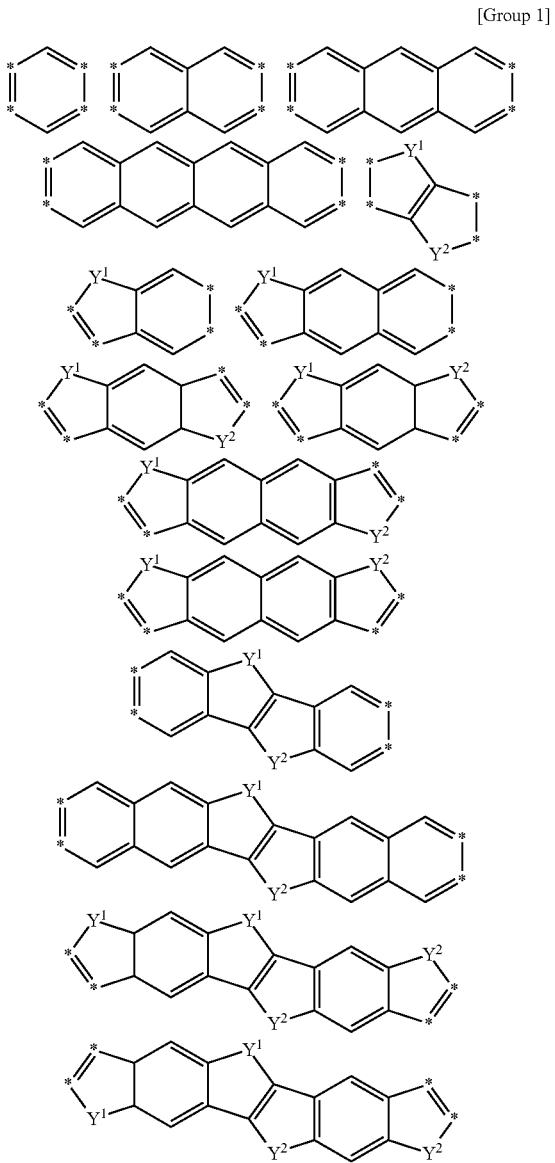

In Group 1,
Y$^1$ and Y$^2$ are independently one of O, S, Se, and Te, and * is a linking point.

Ar$^1$ and Ar$^2$ may be the same.

X$^{11}$ and X$^{21}$ may be the same and X$^{12}$ and X$^{22}$ may be the same.

R$^{11}$ and R$^{21}$ may independently be hydrogen, and R$^{12}$ and R$^{22}$ may be different from each other and independently a substituted or unsubstituted C1 to C30 alkyl group, a substituted or unsubstituted C2 to C30 alkenyl group, a substituted or unsubstituted C2 to C30 alkynyl group, a substituted or unsubstituted C3 to C30 cycloalkyl group, a substituted or unsubstituted C3 to C30 cycloalkenyl group, a substituted or unsubstituted C1 to C30 alkoxy group, a substituted or unsubstituted C3 to C30 heterocycloalkyl group, a substituted or unsubstituted C3 to C30 heterocycloalkenyl group, a substituted or unsubstituted C6 to C30 aryl group, a substituted or unsubstituted C7 to C30 alkylaryl group, a substituted or unsubstituted C6 to C30 aryloxy group, a substituted or unsubstituted C3 to C30 heteroaryl group, a substituted or unsubstituted C4 to C30 alkylheteroaryl group, a halogen, a cyano group, or a combination thereof.

In some embodiments, R$^{11}$ and R$^{21}$ may independently be a substituted or unsubstituted C1 to C30 linear alkyl group, a substituted or unsubstituted C2 to C30 linear alkenyl group, a substituted or unsubstituted C2 to C30 linear alkynyl group, a substituted or unsubstituted C1 to C30 alkoxy group, or a combination thereof, R$^{12}$ and R$^{22}$ may independently be a substituted or unsubstituted C3 to C30 branched alkyl group, a substituted or unsubstituted C3 to C30 branched alkenyl group, a substituted or unsubstituted C3 to C30 branched alkynyl group, or a combination thereof, and R$^{11}$ and R$^{21}$ may be different from each other or R$^{12}$ and R$^{22}$ may be different from each other.

In some embodiments, R$^{11}$ and R$^{21}$ may independently be a substituted or unsubstituted C1 to C30 alkyl group, a substituted or unsubstituted C2 to C30 alkenyl group, a substituted or unsubstituted C2 to C30 alkynyl group, a substituted or unsubstituted C1 to C30 alkoxy group, or a combination thereof, R$^{12}$ and R$^{22}$ may independently be a substituted or unsubstituted C3 to C30 cycloalkyl group, a substituted or unsubstituted C3 to C30 cycloalkenyl group, a substituted or unsubstituted C3 to C30 heterocycloalkyl group, a substituted or unsubstituted C3 to C30 heterocycloalkenyl group, a substituted or unsubstituted C6 to C30 aryl group, a substituted or unsubstituted C7 to C30 alkylaryl group, a substituted or unsubstituted C6 to C30 aryloxy group, a substituted or unsubstituted C3 to C30 heteroaryl group, a substituted or unsubstituted C4 to C30 alkylheteroaryl group, or a combination thereof, and R$^{11}$ and R$^{21}$ may be different from each other or R$^{12}$ and R$^{22}$ may be different from each other.

In some embodiments, R$^{11}$ and R$^{21}$ may independently be a substituted or unsubstituted C3 to C30 cycloalkyl group, a substituted or unsubstituted C3 to C30 cycloalkenyl group, a substituted or unsubstituted C6 to C30 aryl group, or a combination thereof, R$^{12}$ and R$^{22}$ may independently be a substituted or unsubstituted C3 to C30 heterocycloalkyl group, a substituted or unsubstituted C3 to C30 heterocycloalkenyl group, a substituted or unsubstituted C3 to C30 heteroaryl group, a substituted or unsubstituted C4 to C30 alkylheteroaryl group, or a combination thereof, and R$^{11}$ and R$^{21}$ may be different from each other or R$^{12}$ and R$^{22}$ may be different from each other.

In some embodiments, R$^{12}$ and R$^{22}$ may be different from each other and may independently be one of a substituted or unsubstituted C1 to C30 alkyl group, a substituted or unsubstituted C7 to C30 alkylaryl group, and a substituted or unsubstituted C4 to C30 alkylheteroaryl group.

In some embodiments, R$^{22}$ may include an alkyl group having a longer chain than R$^{12}$.

In some embodiments, R$^{11}$ and R$^{21}$ may be the same or different and may independently be one of hydrogen, a substituted or unsubstituted C6 to C30 aryl group, and a substituted or unsubstituted C3 to C30 heteroaryl group.

In some embodiments, the first compound and the second compound may be included in a weight ratio of about 10:90 to about 90:10.

In some embodiments, the organic thin film may further include a third compound and the third compound may be a substituted or unsubstituted fused polycyclic heteroaromatic compound that is different from the first compound and the second compound.

In some embodiments, X$^{11}$, X$^{12}$, X$^{21}$, and X$^{22}$ may be S.

In some embodiments Ar$^1$ and Ar$^2$ may each include at least one substituted or unsubstituted thiophene, and n1 and n2 may be 1.

In some embodiments $Ar^1$ and $Ar^2$ may be the same.

In some embodiments $Ar^1$ and $Ar^2$ may each include two unsubstituted thiophenes.

In some embodiments, the first compound and the second compound may be included in a weight ratio of about 10:90 to about 90:10.

According to another embodiment, an electronic device including the organic thin film is provided.

According to another embodiment, an organic thin film transistor may include a gate electrode, a source electrode and a drain electrode, and an organic semiconductor layer overlapping with the gate electrode. The source electrode and a drain electrode may be electrically connected to the organic semiconductor layer, wherein the organic semiconductor layer may include the first compound represented by one of Chemical Formula 1A and 1B and the second compound different from the first compound and represented by one of Chemical Formula 2A and 2B.

According to another embodiment, an electronic device includes the organic thin film transistor.

Cracks of the organic thin film may be reduced and prevented and thus electrical characteristics may be improved.

DETAILED DESCRIPTION

Figure 1A:
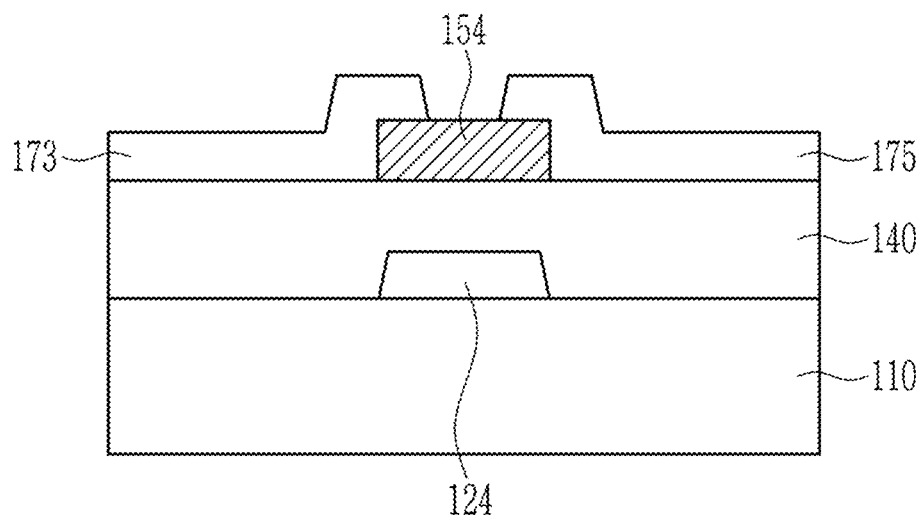
FIGS. 1A to 1C are cross-sectional views showing an organic thin film transistor according to some embodiments.

Example embodiments will hereinafter be described in detail, and may be easily performed by a person having an ordinary skill in the related art. However, this disclosure may be embodied in many different forms and is not to be construed as limited to the embodiments set forth herein.

In the drawings, the thickness of layers, films, panels, regions, etc., are exaggerated for clarity.

It will be understood that when an element such as a layer, film, region, or substrate is referred to as being "on" another element, it may be directly on the other element or intervening elements may also be present. In contrast, when an element is referred to as being "directly on" another element, there are no intervening elements present.

As used herein, when a definition is not otherwise provided, "thin film" is a film or a layer having a thickness of 1 Å to 1,000 μm.

As used herein, when a definition is not otherwise provided, "substituted" may refer to replacement of hydrogen of a compound or a group by a substituent selected from a halogen atom, a hydroxy group, an alkoxy group, a nitro group, a cyano group, an amino group, an azido group, an amidino group, a hydrazino group, a hydrazono group, a carbonyl group, a carbamyl group, a thiol group, an ester group, a carboxyl group or a salt thereof, a sulfonic acid group or a salt thereof, a phosphoric acid or a salt thereof, a C1 to C20 alkyl group, a C2 to C20 alkenyl group, a C2 to C20 alkynyl group, a C6 to C30 aryl group, a C7 to C30 arylalkyl group, a C7 to C30 alkylaryl group, a C1 to C30 alkoxy group, a C1 to C20 heteroalkyl group, a C3 to C20 heteroaryl group, a C3 to C20 heteroarylalkyl group, a C3 to C30 cycloalkyl group, a C3 to C15 cycloalkenyl group, a C6 to C15 cycloalkynyl group, a C3 to C30 heterocycloalkyl group, and a combination thereof.

As used herein, when a definition is not otherwise provided, "hetero" may refer to inclusion of one to four heteroatoms selected from N, O, S, Se, Te, Si, and P.

As used herein, when a definition is not otherwise provided, "alkyl group" may refer to a linear or branched, saturated, monovalent hydrocarbon group (e.g., a methyl group, an ethyl group, a propyl group, an isobutyl group, a sec-butyl group, a tert-butyl group, a pentyl group, an iso-amyl group, a hexyl group, etc.).

As used herein, when a definition is not otherwise provided, "alkenyl group" may refer to a linear or branched, saturated, monovalent hydrocarbon group (e.g., an ethenyl group) having at least one carbon-carbon double bond.

As used herein, when a definition is not otherwise provided, "alkynyl group" may refer to a linear or branched saturated monovalent hydrocarbon group including at least one carbon-carbon triple bond (e.g., an ethynyl group).

As used herein, when a definition is not otherwise provided, "alkoxy group" may refer to an alkyl group that is linked via oxygen, for example a methoxy, an ethoxy, and a sec-butyloxy group.

As used herein, when a definition is not otherwise provided, "aryl group" may refer to a monovalent functional group formed by the removal of one hydrogen atom from one or more rings of an arene, e.g., phenyl, biphenyl, or naphthyl. The arene may refer to a hydrocarbon having an aromatic ring, and includes monocyclic and polycyclic hydrocarbons, wherein the additional ring(s) of the polycyclic hydrocarbon may be aromatic or nonaromatic.

As used herein, when a definition is not otherwise provided, "arylalkyl group" may refer to an alkyl group where at least one hydrogen atom is replaced by an aryl group.

As used herein, when a definition is not otherwise provided, "alkylaryl group" may refer to an aryl group where at least one hydrogen atom is replaced by an alkyl group.

As used herein, when a definition is not otherwise provided, "aryloxy group" may refer to an aryl group that is linked via oxygen, and the aryl group is the same as described above.

As used herein, when a definition is not otherwise provided, "cycloalkyl group" may refer to a monovalent functional group having one or more saturated rings in which all ring members are carbon, e.g., a cyclopentyl group and a cyclohexyl group.

As used herein, when a definition is not otherwise provided, "heteroalkyl group" may refer to the alkyl group defined above where methylene ($-(CH_2)-$) is replaced by $-O-$, $-S-$, $-S(=O)_2-$, $-Se-$, $-Te-$, or $-NR-$ (wherein R is independently hydrogen or a C1 to C10 alkyl group).

As used herein, when a definition is not otherwise provided, "arylheteroalkyl group" may refer to the heteroalkyl group defined above where at least one hydrogen atom is replaced by an aryl group.

As used herein, when a definition is not otherwise provided, "heteroarylalkyl group" may refer to the alkyl group defined above where at least one hydrogen atom is replaced by a heteroaryl group.

As used herein, when a definition is not otherwise provided, "alkylheteroaryl group" may refer to a heteroaryl group where at least one hydrogen atom is replaced by an alkyl group.

As used herein, when a definition is not otherwise provided, "aromatic ring" may refer to a functional group in which all atoms in the cyclic functional group have a p-orbital, and wherein these p-orbitals are conjugated. For example, the aromatic ring may be a C6 to C20 aryl group.

Expressions such as "at least one of," when preceding a list of elements (e.g., A, B, and C), modify the entire list of elements and do not modify the individual elements of the list. For example, "at least one of A, B, and C," "at least one of A, B, or C," "one of A, B, C, or a combination thereof," and "one of A, B, C, and a combination thereof," respectively, may be construed as covering any one of the following combinations: A; B; A and B; A and C; B and C; and A, B, and C.

Hereinafter, an organic thin film according to an embodiment is described.

An organic thin film according to an embodiment includes a plurality of fused polycyclic heteroaromatic compounds, and may include a first compound represented by one of Chemical Formula 1A and 1B and a second compound that is different from the first compound and represented by one of Chemical Formulae 2A and 2B.

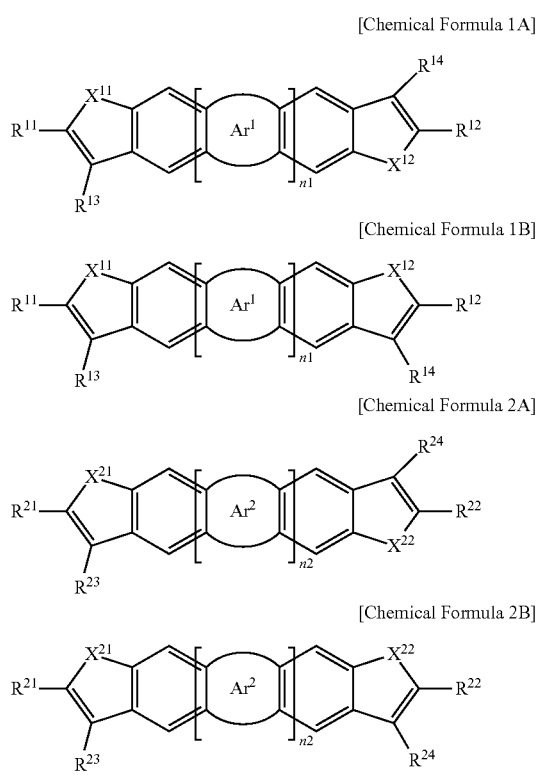

[Chemical Formula 1A]

[Chemical Formula 1B]

[Chemical Formula 2A]

[Chemical Formula 2B]

In Chemical Formulae 1A, 1B, 2A, and 2B, $X^{11}$, $X^{12}$, $X^{21}$, and $X^{22}$ are independently one of O, S, Se, Te, and $NR^a$, $Ar^1$ and $Ar^2$ independently include at least one substituted or unsubstituted benzene ring, at least one substituted or unsubstituted furan ring, at least one substituted or unsubstituted thiophene ring, at least one substituted or unsubstituted selenophene ring, at least one substituted or unsubstituted tellurophene ring, or a fused ring of two or more of the foregoing rings, $R^{11}$ and $R^{12}$ are different from each other or $R^{13}$ and $R^{14}$ are different from each other, $R^{21}$ and $R^{22}$ are different from each other or $R^{23}$ and $R^{24}$ are different from each other, $R^{11}$ to $R^{14}$, $R^{21}$ to $R^{24}$, and $R^a$ are independently hydrogen, a substituted or unsubstituted C1 to C30 alkyl group, a substituted or unsubstituted C2 to C30 alkenyl group, a substituted or unsubstituted C2 to C30 alkynyl group, a substituted or unsubstituted C3 to C30 cycloalkyl group, a substituted or unsubstituted C3 to C30 cycloalkenyl group, a substituted or unsubstituted C1 to C30 alkoxy group, a substituted or unsubstituted C3 to C30 heterocycloalkyl group, a substituted or unsubstituted C3 to C30 heterocycloalkenyl group, a substituted or unsubstituted C6 to C30 aryl group, a substituted or unsubstituted C7 to C30 alkylaryl group, a substituted or unsubstituted C6 to C30 aryloxy group, a substituted or unsubstituted C3 to C30 heteroaryl group, a substituted or unsubstituted C4 to C30 alkylheteroaryl group, a halogen, a cyano group, or a combination thereof, and n1 and n2 are independently 0 or 1.

For example, the first compound and the second compound may be mixed in the organic thin film. For example, the first compound and the second compound may be formed by a codeposition or a solution process using a mixed solution including the first compound and the second compound, but inventive concepts are not limited thereto.

The organic thin film includes the first compound and the second compound having different structures, and thus a film density may be lowered compared with the thin film made of a single material and a degree of freedom of molecules are increased and film flexibility may be effectively improved. Accordingly, generation of cracks on the surface of organic thin film may be effectively reduced or prevented, and thus loss of electrical characteristics due to the cracks may be prevented.

The first compound and the second compound may include the same or different fused polycyclic heteroaromatic rings as a core.

For example, the first compound and the second compound may include the same fused polycyclic heteroaromatic rings as a core.

For example, the first compound and the second compound may include different fused polycyclic heteroaromatic rings as a core.

For example, n1 and/or n2 of Chemical Formulae 1A to 2B may be 0, and thus the first compound and/or the second compound including a core structure of a fused polycyclic aromatic ring in which four rings are fused.

For example, n1 and/or n2 of Chemical Formulae 1A to 2B may be 1, and thus the first compound and/or the second compound including a core structure of a fused polycyclic aromatic ring in which five or more rings are fused. For example, the first compound and/or the second compound may be a fused polycyclic aromatic compound including a core structure of a fused polycyclic aromatic ring in which five to twelve rings are fused. For example, the first compound and/or the second compound may be a fused polycyclic aromatic compound including a core structure of a fused polycyclic aromatic ring in which five to ten rings are fused.

For example, $Ar^1$ and $Ar^2$ of Chemical Formulae 1A to 2B may independently include one to eight rings, for example one to six rings and may for example independently include a substituted or unsubstituted benzene ring; a substituted or unsubstituted furan ring; a substituted or unsubstituted thiophene ring; a substituted or unsubstituted selenophene ring; a substituted or unsubstituted tellurophene ring; a substituted or unsubstituted naphthalene ring; a substituted or unsubstituted anthracene ring; a substituted or unsubstituted tetracene ring; a fused ring of at least one substituted or unsubstituted benzene ring and at least one substituted or unsubstituted furan ring; a fused ring of at least one substituted or unsubstituted benzene ring and at least one substituted or unsubstituted thiophene ring; a fused ring of at least one substituted or unsubstituted benzene ring and at least one substituted or unsubstituted selenophene ring; a fused ring of at least one substituted or unsubstituted benzene ring and at least one substituted or unsubstituted tellurophene ring; a fused ring of at least two substituted or unsubstituted furan rings; a fused ring of at least two substituted or unsubstituted thiophene rings; a fused ring of at least two substituted or unsubstituted selenophene rings; a fused ring of at least two substituted or unsubstituted tellurophene rings; a fused ring of at least one substituted or unsubstituted furan ring and at least one substituted or unsubstituted thiophene ring; a fused ring of at least one substituted or unsubstituted furan ring and at least one substituted or unsubstituted selenophene ring; a fused ring of at least one substituted or unsubstituted furan ring and at least one substituted or unsubstituted tellurophene ring; a fused ring of at least one substituted or unsubstituted thiophene ring and at least one substituted or unsubstituted selenophene ring; a fused ring of at least one substituted or unsubstituted thiophene ring and at least one substituted or unsubstituted tellurophene ring; or a fused ring of at least one substituted or unsubstituted selenophene ring and at least one substituted or unsubstituted tellurophene ring, but are not limited thereto.

For example, $Ar^1$ and $Ar^2$ of Chemical Formulae 1A to 2B may independently include at least one of a substituted or unsubstituted furan ring, a substituted or unsubstituted thiophene ring, a substituted or unsubstituted selenophene ring, and substituted or unsubstituted tellurophene ring.

For example, $Ar^1$ and $Ar^2$ may independently be one of substituted or unsubstituted rings of Group 1, but are not limited thereto.

[Group 1]

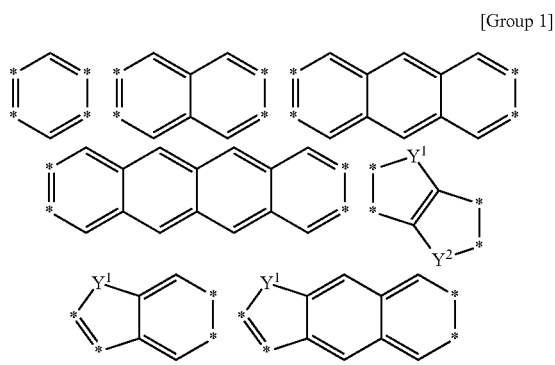
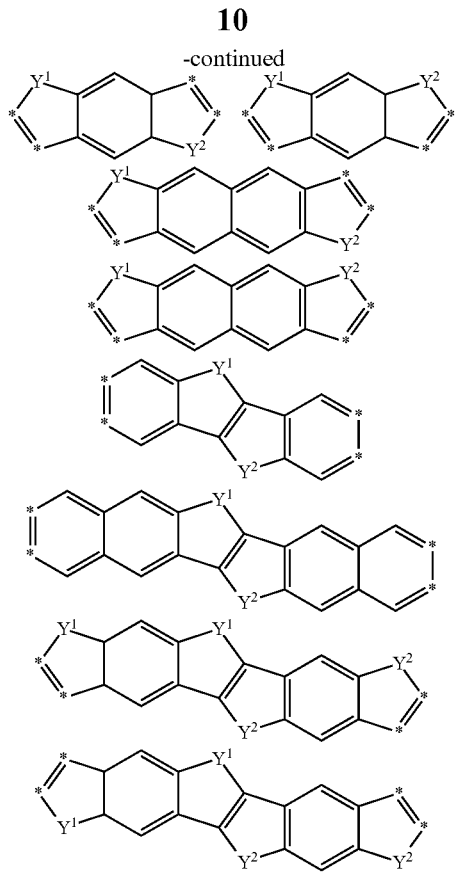

In Group 1, $Y^1$ and $Y^2$ are independently one of O, S, Se, and Te, and * is a linking point.

For example, in each ring of Group 1, $Y^1$ and $Y^2$ may be the same.

For example, $Y^1$ and $Y^2$ may independently be O.
For example, $Y^1$ and $Y^2$ may independently be S.
For example, $Y^1$ and $Y^2$ may independently be Se.
For example, $Y^1$ and $Y^2$ may independently be Te.
For example, in each ring of Group 1, $Y^1$ and $Y^2$ may be different from each other.

For example, one of $Y^1$ and $Y^2$ may be S and the other of $Y^1$ and $Y^2$ may be 0.

For example, one of $Y^1$ and $Y^2$ may be 0 or S and the other of $Y^1$ and $Y^2$ may be Se or Te.

For example, one of $Y^1$ and $Y^2$ may be Se and the other of $Y^1$ and $Y^2$ may be Te.

For example, $Ar^1$ and $Ar^2$ of Chemical Formulae 1A to 2B may be the same.

For example, In Chemical Formulae 1A to 2B, $Ar^1$ and $Ar^2$ may be the same, $X^{11}$ and $X^{21}$ may be the same, and $X^{12}$ and $X^{22}$ may be the same. The first compound and the second compound may include a fused polycyclic heteroaromatic rings having the same structure as a core.

The first compound may have at least one substituent bound to the fused polycyclic heteroaromatic ring and at least one of the substituents may be positioned asymmetrically. Herein, 'asymmetrically positioned' means that they do not have the same substituents at the positions corresponding to each other in the center of the fused polycyclic heteroaromatic ring.

For example, in Chemical Formula 1A or 1B, $R^{11}$ and $R^{12}$ may be different from each other or $R^{13}$ and $R^{14}$ may be different from each other.

For example, $R^{11}$ and $R^{12}$ may be different from each other.

For example, $R^{13}$ and $R^{14}$ may be different from each other.

For example, $R^{11}$ and $R^{12}$ may be different from each other and $R^{13}$ and $R^{14}$ may be the same.

For example, $R^{13}$ and $R^{14}$ may be different from each other and $R^{11}$ and $R^{12}$ may be the same.

For example, $R^{11}$ and $R^{12}$ may be different from each other or $R^{13}$ and $R^{14}$ may be same.

The second compound may have at least one substituent bound to the fused polycyclic aromatic ring and at least one of the substituents may be positioned asymmetrically.

For example, in Chemical Formula 2A or 2B, $R^{21}$ and $R^{22}$ may be different from each other and $R^{23}$ and $R^{24}$ may be different from each other.

For example, $R^{21}$ and $R^{22}$ may be different from each other.

For example, $R^{23}$ and $R^{24}$ may be different from each other.

For example, $R^{21}$ and $R^{22}$ may be different from each other and $R^{23}$ and $R^{24}$ may be the same.

For example, $R^{23}$ and $R^{24}$ may be different from each other and $R^{21}$ and $R^{22}$ may be the same.

For example, $R^{21}$ and $R^{22}$ may be different from each other and $R^{23}$ and $R^{24}$ may be different from each other.

The fused polycyclic aromatic compound having an asymmetrically positioned substituent may exhibit liquid crystallinity in a desired (and/or alternatively predetermined) temperature range, and thus a degree of alignment of the molecules may be increased during heat treatment, and charge mobility of the organic thin film may be improved. The liquid crystallinity may be, for example, a smectic liquid crystallinity, and may be, for example, a smectic liquid crystallinity and a nematic liquid crystallinity. This liquid crystallinity is shown in a relatively low temperature range, and thus the process temperature may be lowered. For example, the first compound and the second compound may respectively exhibit liquid crystallinity at a temperature of less than or equal to about 400° C., for example about 150° C. to about 350° C., about 180° C. to about 300° C., or about 200° C. to about 280° C. In addition, additional annealing at a desired (and/or alternatively predetermined) temperature may further increase a degree of alignment of the molecules, thereby further improving charge mobility of the organic thin film including the first compound and the second compound.

For example, the first compound and/or the second compound may have a substituent at one side alone of the fused polycyclic aromatic ring.

For example, in Chemical Formula 1A or 1B, $R^{11}$ may be hydrogen and $R^{12}$ may be a substituted or unsubstituted C1 to C30 alkyl group, a substituted or unsubstituted C2 to C30 alkenyl group, a substituted or unsubstituted C2 to C30 alkynyl group, a substituted or unsubstituted C3 to C30 cycloalkyl group, a substituted or unsubstituted C3 to C30 cycloalkenyl group, a substituted or unsubstituted C1 to C30 alkoxy group, a substituted or unsubstituted C3 to C30 heterocycloalkyl group, a substituted or unsubstituted C3 to C30 heterocycloalkenyl group, a substituted or unsubstituted C6 to C30 aryl group, a substituted or unsubstituted C7 to C30 alkylaryl group, a substituted or unsubstituted C6 to C30 aryloxy group, a substituted or unsubstituted C3 to C30 heteroaryl group, a substituted or unsubstituted C4 to C30 alkylheteroaryl group, a halogen, a cyano group, or a combination thereof.

For example, in Chemical Formula 1A or 1B, $R^{13}$ may be hydrogen and $R^{14}$ may be a substituted or unsubstituted C1 to C30 alkyl group, a substituted or unsubstituted C2 to C30 alkenyl group, a substituted or unsubstituted C2 to C30 alkynyl group, a substituted or unsubstituted C3 to C30 cycloalkyl group, a substituted or unsubstituted C3 to C30 cycloalkenyl group, a substituted or unsubstituted C1 to C30 alkoxy group, a substituted or unsubstituted C3 to C30 heterocycloalkyl group, a substituted or unsubstituted C3 to C30 heterocycloalkenyl group, a substituted or unsubstituted C6 to C30 aryl group, a substituted or unsubstituted C7 to C30 alkylaryl group, a substituted or unsubstituted C6 to C30 aryloxy group, a substituted or unsubstituted C3 to C30 heteroaryl group, a substituted or unsubstituted C4 to C30 alkylheteroaryl group, a halogen, a cyano group, or a combination thereof.

For example, in Chemical Formula 2A or 2B, $R^{21}$ may be hydrogen and $R^{22}$ may be a substituted or unsubstituted C1 to C30 alkyl group, a substituted or unsubstituted C2 to C30 alkenyl group, a substituted or unsubstituted C2 to C30 alkynyl group, a substituted or unsubstituted C3 to C30 cycloalkyl group, a substituted or unsubstituted C3 to C30 cycloalkenyl group, a substituted or unsubstituted C1 to C30 alkoxy group, a substituted or unsubstituted C3 to C30 heterocycloalkyl group, a substituted or unsubstituted C3 to C30 heterocycloalkenyl group, a substituted or unsubstituted C6 to C30 aryl group, a substituted or unsubstituted C7 to C30 alkylaryl group, a substituted or unsubstituted C6 to C30 aryloxy group, a substituted or unsubstituted C3 to C30 heteroaryl group, a substituted or unsubstituted C4 to C30 alkylheteroaryl group, a halogen, a cyano group, or a combination thereof.

For example, in Chemical Formula 2A or 2B, $R^{23}$ may be hydrogen and $R^{24}$ may be a substituted or unsubstituted C1 to C30 alkyl group, a substituted or unsubstituted C2 to C30 alkenyl group, a substituted or unsubstituted C2 to C30 alkynyl group, a substituted or unsubstituted C3 to C30 cycloalkyl group, a substituted or unsubstituted C3 to C30 cycloalkenyl group, a substituted or unsubstituted C1 to C30 alkoxy group, a substituted or unsubstituted C3 to C30 heterocycloalkyl group, a substituted or unsubstituted C3 to C30 heterocycloalkenyl group, a substituted or unsubstituted C6 to C30 aryl group, a substituted or unsubstituted C7 to C30 alkylaryl group, a substituted or unsubstituted C6 to C30 aryloxy group, a substituted or unsubstituted C3 to C30 heteroaryl group, a substituted or unsubstituted C4 to C30 alkylheteroaryl group, a halogen, a cyano group, or a combination thereof.

For example, the first compound and/or the second compound may have a linear substituent at one side of the fused polycyclic aromatic ring and a nonlinear substituent at the other side thereof.

For example, in Chemical Formula 1A or 1B, $R^{11}$ may be a substituted or unsubstituted C1 to C30 linear alkyl group, a substituted or unsubstituted C2 to C30 linear alkenyl group, a substituted or unsubstituted C2 to C30 linear alkynyl group, a substituted or unsubstituted C1 to C30 alkoxy group, or a combination thereof and $R^{12}$ may be a substituted or unsubstituted C3 to C30 branched alkyl group, a substituted or unsubstituted C3 to C30 branched alkenyl group, a substituted or unsubstituted C3 to C30 branched alkynyl group, or a combination thereof.

For example, in Chemical Formula 1A or 1B, $R^{13}$ may be a substituted or unsubstituted C1 to C30 linear alkyl group, a substituted or unsubstituted C2 to C30 linear alkenyl group, a substituted or unsubstituted C2 to C30 linear alkynyl group, a substituted or unsubstituted C1 to C30 alkoxy group, or a combination thereof and $R^{14}$ may be a substituted or unsubstituted C3 to C30 branched alkyl group, a substituted or unsubstituted C3 to C30 branched alkenyl group, a substituted or unsubstituted C3 to C30 branched alkynyl group, or a combination thereof.

For example, in Chemical Formula 2A or 2B, $R^{21}$ may be a substituted or unsubstituted C1 to C30 linear alkyl group, a substituted or unsubstituted C2 to C30 linear alkenyl group, a substituted or unsubstituted C2 to C30 linear alkynyl group, a substituted or unsubstituted C1 to C30 alkoxy group, or a combination thereof and $R^{22}$ may be a substituted or unsubstituted C3 to C30 branched alkyl group, a substituted or unsubstituted C3 to C30 branched alkenyl group, a substituted or unsubstituted C3 to C30 branched alkynyl group, or a combination thereof.

For example, in Chemical Formula 2A or 2B, $R^{23}$ may be a substituted or unsubstituted C1 to C30 linear alkyl group, a substituted or unsubstituted C2 to C30 linear alkenyl group, a substituted or unsubstituted C2 to C30 linear alkynyl group, a substituted or unsubstituted C1 to C30 alkoxy group, or a combination thereof and $R^{24}$ may be a substituted or unsubstituted C3 to C30 branched alkyl group, a substituted or unsubstituted C3 to C30 branched alkenyl group, a substituted or unsubstituted C3 to C30 branched alkynyl group, or a combination thereof.

For example, the first compound and/or the second compound may have a non-cyclic substituent at one side of the fused polycyclic aromatic ring and a cyclic substituent at the other side thereof.

For example, in Chemical Formula 1A or 1B, $R^{11}$ may be a substituted or unsubstituted C1 to C30 alkyl group, a substituted or unsubstituted C2 to C30 alkenyl group, a substituted or unsubstituted C2 to C30 alkynyl group, a substituted or unsubstituted C1 to C30 alkoxy group, or a combination thereof and $R^{12}$ may be a substituted or unsubstituted C3 to C30 cycloalkyl group, a substituted or unsubstituted C3 to C30 cycloalkenyl group, a substituted or unsubstituted C3 to C30 heterocycloalkyl group, a substituted or unsubstituted C3 to C30 heterocycloalkenyl group, a substituted or unsubstituted C6 to C30 aryl group, a substituted or unsubstituted C7 to C30 alkylaryl group, a substituted or unsubstituted C6 to C30 aryloxy group, a substituted or unsubstituted C3 to C30 heteroaryl group, a substituted or unsubstituted C4 to C30 alkylheteroaryl group, or a combination thereof.

For example, in Chemical Formula 1A or 1B, $R^{13}$ may be a substituted or unsubstituted C1 to C30 alkyl group, a substituted or unsubstituted C2 to C30 alkenyl group, a substituted or unsubstituted C2 to C30 alkynyl group, a substituted or unsubstituted C1 to C30 alkoxy group, or a combination thereof and $R^{14}$ may be a substituted or unsubstituted C3 to C30 cycloalkyl group, a substituted or unsubstituted C3 to C30 cycloalkenyl group, a substituted or unsubstituted C3 to C30 heterocycloalkyl group, a substituted or unsubstituted C3 to C30 heterocycloalkenyl group, a substituted or unsubstituted C6 to C30 aryl group, a substituted or unsubstituted C7 to C30 alkylaryl group, a substituted or unsubstituted C6 to C30 aryloxy group, a substituted or unsubstituted C3 to C30 heteroaryl group, a substituted or unsubstituted C4 to C30 alkylheteroaryl group, or a combination thereof.

For example, in Chemical Formula 2A or 2B, $R^{21}$ may be a substituted or unsubstituted C1 to C30 alkyl group, a substituted or unsubstituted C2 to C30 alkenyl group, a substituted or unsubstituted C2 to C30 alkynyl group, a substituted or unsubstituted C1 to C30 alkoxy group, or a combination thereof and $R^{22}$ may be a substituted or unsubstituted C3 to C30 cycloalkyl group, a substituted or unsubstituted C3 to C30 cycloalkenyl group, a substituted or unsubstituted C3 to C30 heterocycloalkyl group, a substituted or unsubstituted C3 to C30 heterocycloalkenyl group, a substituted or unsubstituted C6 to C30 aryl group, a substituted or unsubstituted C7 to C30 alkylaryl group, a substituted or unsubstituted C6 to C30 aryloxy group, a substituted or unsubstituted C3 to C30 heteroaryl group, a substituted or unsubstituted C4 to C30 alkylheteroaryl group, or a combination thereof.

For example, in Chemical Formula 2A or 2B, $R^{23}$ may be a substituted or unsubstituted C1 to C30 alkyl group, a substituted or unsubstituted C2 to C30 alkenyl group, a substituted or unsubstituted C2 to C30 alkynyl group, a substituted or unsubstituted C1 to C30 alkoxy group, or a combination thereof and $R^{24}$ may be a substituted or unsubstituted C3 to C30 cycloalkyl group, a substituted or unsubstituted C3 to C30 cycloalkenyl group, a substituted or unsubstituted C3 to C30 heterocycloalkyl group, a substituted or unsubstituted C3 to C30 heterocycloalkenyl group, a substituted or unsubstituted C6 to C30 aryl group, a substituted or unsubstituted C7 to C30 alkylaryl group, a substituted or unsubstituted C6 to C30 aryloxy group, a substituted or unsubstituted C3 to C30 heteroaryl group, a substituted or unsubstituted C4 to C30 alkylheteroaryl group, or a combination thereof.

For example, the first compound and/or the second compound may have a cyclic substituent at one side of the fused polycyclic aromatic ring and a heterocyclic substituent at the other side thereof.

For example, in Chemical Formula 1A or 1B, $R^{11}$ may be a substituted or unsubstituted C3 to C30 cycloalkyl group, a substituted or unsubstituted C3 to C30 cycloalkenyl group, a substituted or unsubstituted C6 to C30 aryl group, a substituted or unsubstituted C7 to C30 alkylaryl group, or a combination thereof and $R^{12}$ may be a substituted or unsubstituted C3 to C30 heterocycloalkyl group, a substituted or unsubstituted C3 to C30 heterocycloalkenyl group, a substituted or unsubstituted C3 to C30 heteroaryl group, a substituted or unsubstituted C4 to C30 alkylheteroaryl group, or a combination thereof.

For example, in Chemical Formula 1A or 1B, $R^{13}$ may be a substituted or unsubstituted C3 to C30 cycloalkyl group, a substituted or unsubstituted C3 to C30 cycloalkenyl group, a substituted or unsubstituted C6 to C30 aryl group, a substituted or unsubstituted C7 to C30 alkylaryl group, or a combination thereof and $R^{14}$ may be a substituted or unsubstituted C3 to C30 heterocycloalkyl group, a substituted or unsubstituted C3 to C30 heterocycloalkenyl group, a substituted or unsubstituted C3 to C30 heteroaryl group, a substituted or unsubstituted C4 to C30 alkylheteroaryl group, or a combination thereof.

For example, in Chemical Formula 2A or 2B, $R^{21}$ may be a substituted or unsubstituted C3 to C30 cycloalkyl group, a substituted or unsubstituted C3 to C30 cycloalkenyl group, a substituted or unsubstituted C6 to C30 aryl group, a substituted or unsubstituted C7 to C30 alkylaryl group, or a combination thereof and $R^{22}$ may be a substituted or unsubstituted C3 to C30 heterocycloalkyl group, a substituted or unsubstituted C3 to C30 heterocycloalkenyl group, a substituted or unsubstituted C3 to C30 heteroaryl group, a substituted or unsubstituted C4 to C30 alkylheteroaryl group, or a combination thereof.

For example, in Chemical Formula 2A or 2B, $R^{23}$ may be a substituted or unsubstituted C3 to C30 cycloalkyl group, a substituted or unsubstituted C3 to C30 cycloalkenyl group, a substituted or unsubstituted C6 to C30 aryl group, a substituted or unsubstituted C7 to C30 alkylaryl group, or a combination thereof and $R^{24}$ may be a substituted or unsubstituted C3 to C30 heterocycloalkyl group, a substituted or unsubstituted C3 to C30 heterocycloalkenyl group, a substituted or unsubstituted C3 to C30 heteroaryl group, a substituted or unsubstituted C4 to C30 alkylheteroaryl group, or a combination thereof.

At least one substituent of the first compound may be different from at least one substituent of the second compound.

For example, $R^{11}$ of Chemical Formula 1A or 1B may be different from $R^{21}$ of Chemical Formula 2A or 2B.

For example, $R^{12}$ of Chemical Formula 1A or 1B may be different from $R^{22}$ of Chemical Formula 2A or 2B.

For example, $R^{11}$ of Chemical Formula 1A or 1B may be same as $R^{21}$ of Chemical Formula 2A or 2B and $R^{12}$ of Chemical Formula 1A or 1B may be different from $R^{22}$ of Chemical Formula 2A or 2B.

For example, $R^{12}$ of Chemical Formula 1A or 1B may be the same as $R^{22}$ of Chemical Formula 2A or 2B and $R^{11}$ of Chemical Formula 1A or 1B may be different from $R^{12}$ of Chemical Formula 2A or 2B.

For example, $R^{11}$ of Chemical Formula 1A or 1B may be different from $R^{21}$ of Chemical Formula 2A or 2B and $R^{12}$ of Chemical Formula 1A or 1B may be different from $R^{22}$ of Chemical Formula 2A or 2B.

For example, $R^{11}$ of Chemical Formula 1A or 1B and $R^{21}$ of Chemical Formula 2A or 2B may independently be hydrogen, $R^{12}$ of Chemical Formula 1A or 1B and $R^{22}$ of Chemical Formula 2A or 2B may be different and may independently be a substituted or unsubstituted C1 to C30 alkyl group, a substituted or unsubstituted C2 to C30 alkenyl group, a substituted or unsubstituted C2 to C30 alkynyl group, a substituted or unsubstituted C3 to C30 cycloalkyl group, a substituted or unsubstituted C3 to C30 cycloalkenyl group, a substituted or unsubstituted C1 to C30 alkoxy group, a substituted or unsubstituted C3 to C30 heterocycloalkyl group, a substituted or unsubstituted C3 to C30 heterocycloalkenyl group, a substituted or unsubstituted C6 to C30 aryl group, a substituted or unsubstituted C7 to C30 alkylaryl group, a substituted or unsubstituted C6 to C30 aryloxy group, a substituted or unsubstituted C3 to C30 heteroaryl group, a substituted or unsubstituted C4 to C30 alkylheteroaryl group, a halogen, a cyano group, or a combination thereof.

For example, $R^{11}$ of Chemical Formula 1A or 1B and $R^{21}$ of Chemical Formula 2A or 2B may independently be a substituted or unsubstituted C1 to C30 linear alkyl group, a substituted or unsubstituted C2 to C30 linear alkenyl group, a substituted or unsubstituted C2 to C30 linear alkynyl group, a substituted or unsubstituted C1 to C30 alkoxy group, or a combination thereof, $R^{12}$ of Chemical Formula 1A or 1B and $R^{22}$ of Chemical Formula 2A or 2B may independently be a substituted or unsubstituted C3 to C30 branched alkyl group, a substituted or unsubstituted C3 to C30 branched alkenyl group, a substituted or unsubstituted C3 to C30 branched alkynyl group, or a combination thereof, and $R^{11}$ and $R^{21}$ may be different from each other or $R^{12}$ and $R^{22}$ may be different from each other.

For example, $R^{11}$ of Chemical Formula 1A or 1B and $R^{21}$ of Chemical Formula 2A or 2B may independently be a substituted or unsubstituted C1 to C30 alkyl group, a substituted or unsubstituted C2 to C30 alkenyl group, a substituted or unsubstituted C2 to C30 alkynyl group, a substituted or unsubstituted C1 to C30 alkoxy group, or a combination thereof, $R^{12}$ of Chemical Formula 1A or 1B and $R^{22}$ of Chemical Formula 2A or 2B may independently be a substituted or unsubstituted C3 to C30 cycloalkyl group, a substituted or unsubstituted C3 to C30 cycloalkenyl group, a substituted or unsubstituted C3 to C30 heterocycloalkyl group, a substituted or unsubstituted C3 to C30 heterocycloalkenyl group, a substituted or unsubstituted C6 to C30 aryl group, a substituted or unsubstituted C7 to C30 alkylaryl group, a substituted or unsubstituted C6 to C30 aryloxy group, a substituted or unsubstituted C3 to C30 heteroaryl group, a substituted or unsubstituted C4 to C30 alkylheteroaryl group, or a combination thereof, and $R^{11}$ and $R^{21}$ may be different from each other or $R^{12}$ and $R^{22}$ may be different from each other.

For example, $R^{11}$ of Chemical Formula 1A or 1B and $R^{21}$ of Chemical Formula 2A or 2B may independently be a substituted or unsubstituted C3 to C30 cycloalkyl group, a substituted or unsubstituted C3 to C30 cycloalkenyl group, a substituted or unsubstituted C6 to C30 aryl group, or a combination thereof, $R^{12}$ of Chemical Formula 1A or 1B and $R^{22}$ of Chemical Formula 2A or 2B may independently be a substituted or unsubstituted C3 to C30 heterocycloalkyl group, a substituted or unsubstituted C3 to C30 heterocycloalkenyl group, a substituted or unsubstituted C3 to C30 heteroaryl group, a substituted or unsubstituted C4 to C30 alkylheteroaryl group, or a combination thereof, and $R^{11}$ and $R^{21}$ may be different from each other or $R^{12}$ and $R^{22}$ may be different from each other.

For example, at least one substituent of the first compound and at least one substituent of the second compound may independently be one of a substituted or unsubstituted C1 to C30 alkyl group, a substituted or unsubstituted C7 to C30 alkylaryl group, and a substituted or unsubstituted C4 to C30 alkylheteroaryl group wherein the alkyl group included in the substituent of the first compound and the alkyl group included in the substituent of the second compound may have a different chain length.

For example, $R^{12}$ of Chemical Formula 1A or 1B and $R^{22}$ of Chemical Formula 2A or 2B may independently be one of a substituted or unsubstituted C1 to C30 alkyl group, a substituted or unsubstituted C7 to C30 alkylaryl group, and a substituted or unsubstituted C4 to C30 alkylheteroaryl group wherein $R^{22}$ may include an alkyl group having a longer chain than $R^{12}$. For example, the alkyl group included in $R^{12}$ and $R^{22}$ may independently be a C3 to C20 alkyl group, a C6 to C20 alkyl group, or a C8 to C20 alkyl group, wherein $R^{22}$ may include an alkyl group having a longer chain than $R^{12}$. Herein, For example, $R^{11}$ of Chemical Formula 1A or 1B and $R^{21}$ of Chemical Formula 2A or 2B may be the same or different and may independently be one of hydrogen, a substituted or unsubstituted C6 to C30 aryl group, and a substituted or unsubstituted C3 to C30 heteroaryl group.

For example, in Chemical Formula 1A or 1B, $R^{13}$ and $R^{14}$ may independently hydrogen and the first compound may be represented by Chemical Formula 1A-1 or 1B-1.

[Chemical Formula 1A-1]

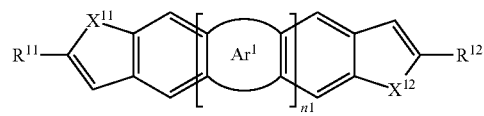

[Chemical Formula 1B-1]

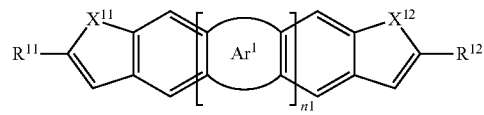

In Chemical Formula 1A-1 or 1B-1,
$X^{11}$, $X^{12}$, $Ar^1$, and $n_1$ are the same as described above, and
$R^{11}$ and $R^{12}$ are different from each other and are the same as described above.

For example, in Chemical Formula 2A or 2B, $R^{23}$ and $R^{24}$ may independently hydrogen and the second compound may be represented by Chemical Formula 2A-1 or 2B-1.

[Chemical Formula 2A-1]

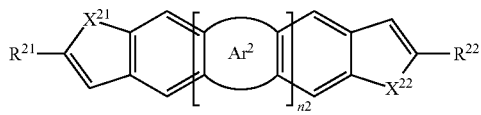

[Chemical Formula 2B-1]

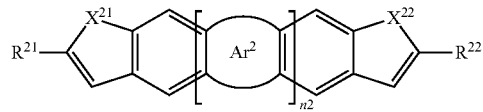

In Chemical Formula 2A-1 or 2B-1,
$X^{21}$, $X^{22}$, $Ar^2$, and n2 are the same as described above, and
$R^{21}$ and $R^{22}$ are different from each other and are the same as described above.

For example, the first compound may be one of compounds of Group 2, but is not limited thereto.

[Group 2]

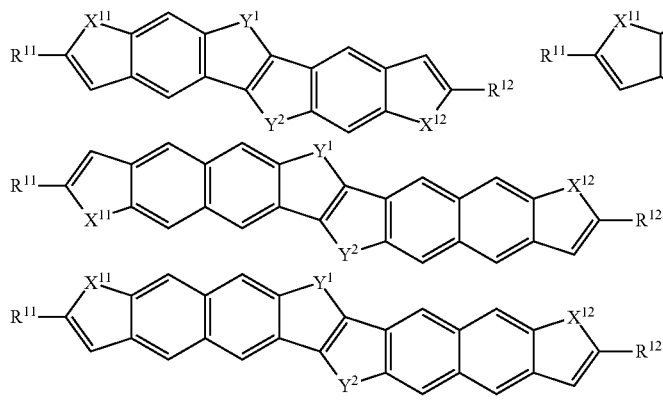

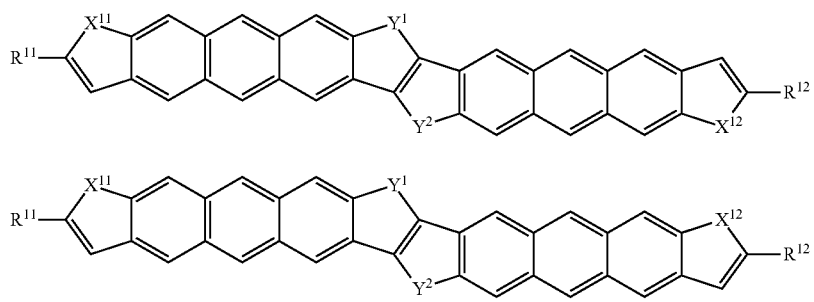

In Group 2, definitions of $X^{11}$, $X^{12}$, $Y^1$, and $Y^2$ are the same as described above, and
$R^{11}$ and $R^{12}$ are different from each other and are the same as described above.

For example, the second compound may be one of compounds of Group 3, but is not limited thereto.

[Group 3]

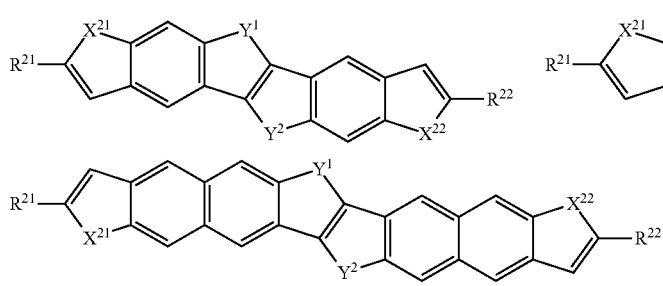

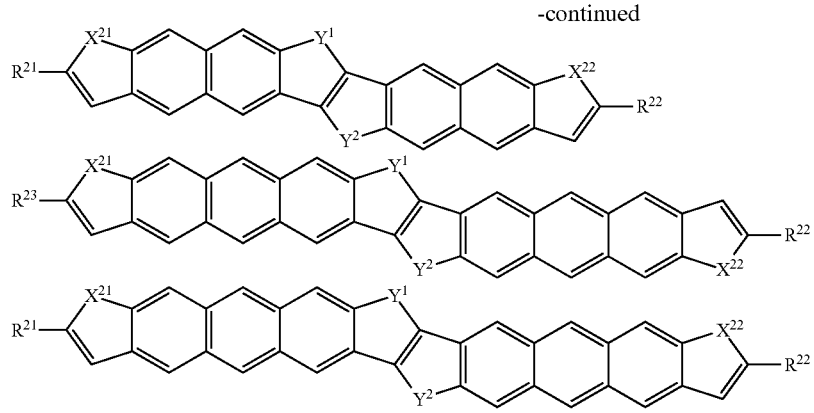

In Group 3, definitions of $X^{21}$, $X^{22}$, $Y^1$, and $Y^2$ are the same as described above, and $R^{21}$ and $R^{22}$ may be different from each other and may be the same as described above.

$R^{11}$ and $R^{21}$ may be different from each other and $R^{12}$ and $R^{22}$ may be different from each other.

For example, in Groups 2 and 3, $R^{11}$ and $R^{12}$ may independently be one of hydrogen, a substituted or unsubstituted C6 to C30 aryl group, and a substituted or unsubstituted C3 to C30 heteroaryl group, $R^{12}$ and $R^{22}$ may independently be one of a substituted or unsubstituted C1 to C30 alkyl group, a substituted or unsubstituted C7 to C30 alkylaryl group, and a substituted or unsubstituted C4 to C30 alkylheteroaryl group, and $R^{22}$ may include an alkyl group having a longer chain than $R^{12}$.

The first compound and the second compound may be included in various ratios in the organic thin film, for example the first compound and the second compound may be included in a weight ratio of about 10:90 to about 90:10, for example about 20:80 to about 80:20, about 30:70 to about 70:30, about 40:60 to about 60:40, or about 50:50.

A composition ratio of the first compound and the second compound may be different in a thickness direction of the organic thin film, and for example, the composition ratio of the first compound and the second compound may be changed stepwise and continuously or discontinuously.

The organic thin film may be formed by codepositing the first compound and the second compound. For example, a first deposition crucible including the first compound and a second deposition crucible including the second compound are prepared in a vacuum evaporation apparatus, a temperature of a substrate is raised to a desired (and/or alternatively predetermined) temperature, and then the first deposition crucible and the second deposition crucible are heated. Codeposition may be started by opening a main shutter when the first compound and the second compound reach a desired (and/or alternatively predetermined) deposition rate. Herein, the temperature of the substrate may be for example about 50° C. to about 250° C. and deposition rates of the first compound and the second compound may independently be about 0.01 Å/s to about 1.0 Å/s.

By setting the deposition rate of the first compound and the second compound to a desired value, the ratio of the first compound to the second compound in the co-deposition may be controlled. A composition ratio of the first compound and the second compound may be changed in a thickness direction of the organic thin film by changing the deposition rate of the first compound and/or the second compound during the codeposition. The composition ratio of the first compound and the second compound in a thickness direction of the organic thin film may be changed stepwise and may be changed continuously or discontinuously. The codeposition may be completed by closing the main shutter at a time at which the required film thickness is reached, and subsequent heat treatment may be performed in a hot plate or an oven.

The organic thin film may be formed by a solution process from a solution including the first compound and the second compound. The first compound and the second compound may be dissolved in respective solvents and may be prepared as a first solution and a second solution to prepare a mixed solution. Alternatively, the first compound and the second compound may be simultaneously dissolved to prepare a mixed solution. The solution process may be for example spin coating, slit coating, inkjet printing, or dip coating, but is not limited thereto.

The organic thin film may further include other third compound that is different from the first compound and the second compound. The third compound may be, for example a substituted or unsubstituted fused polycyclic heteroaromatic compound.

The organic thin film may be an organic semiconductor thin film and be applied to various electronic devices. For example, the compound may be applied to an organic thin film transistor and may be applied to a charge transport layer and/or an active layer of an electronic device such as a solar cell, an organic light emitting diode (OLED) display, and an organic sensor.

Hereinafter, one example of an organic thin film transistor including the compound is described referring to the drawing.

In the drawings, the thickness of layers, films, panels, regions, etc., are exaggerated for clarity. Like reference numerals designate like elements throughout the specification. It will be understood that when an element such as a layer, film, region, or substrate is referred to as being "on" another element, it can be directly on the other element or intervening elements may also be present. In contrast, when an element is referred to as being "directly on" another element, there are no intervening elements present.

Figure 1B:
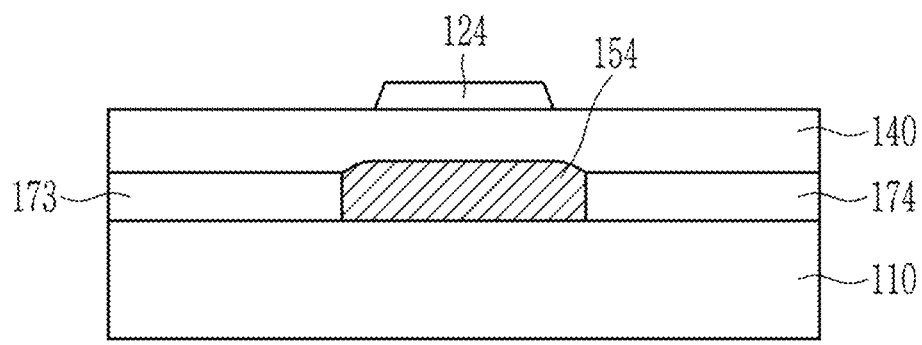
Figure 1C:
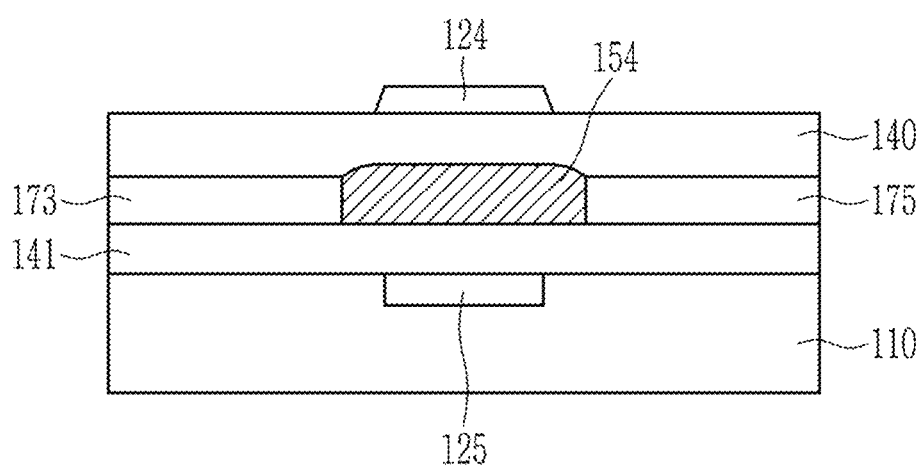

FIGS. 1A to 1C are cross-sectional views showing an organic thin film transistor according to embodiments.

Referring to FIG. 1A, an organic thin film transistor according to embodiment includes a substrate 110; a gate electrode 124 formed on the substrate 110; a gate insulating layer 140 formed on the gate electrode 124; an organic semiconductor layer 154 formed on the gate insulating layer 140; and a source electrode 173 and a drain electrode 175 formed on the organic semiconductor layer 154.

A gate electrode 124 is formed on a substrate 110 made of transparent glass, silicon, or plastic. The gate electrode 124 is connected to a gate line (not shown) transferring a gate signal. The gate electrode 124 may be made of a metal and/or metal alloy. For example, the gate electrode 124 may be made of gold (Au), copper (Cu), nickel (Ni), aluminum (Al), molybdenum (Mo), chromium (Cr), tantalum (Ta), titanium (Ti), an alloy thereof, or a combination thereof.

A gate insulating layer 140 is formed on the gate electrode 124. The gate insulating layer 140 may be made of an organic material and/or an inorganic material. Examples of the organic material may include a soluble polymer compound such as a polyvinyl alcohol-based compound, a polyimide-based compound, a polyacryl-based compound, a polystyrene-based compound, and benzocyclobutane (BCB), and examples of the inorganic material may include a silicon nitride ($SiN_x$) and a silicon oxide ($SiO_2$).

An organic semiconductor layer 154 is formed on the gate insulating layer 140. The organic semiconductor layer 154 may be the aforementioned organic thin film.

A source electrode 173 and a drain electrode 175 are formed on organic semiconductor layer 154. The source electrode 173 and the drain electrode 175 face each other on the organic semiconductor layer 154. The source electrode 173 is electrically connected to the data line (not shown) transferring the data signal. The source electrode 173 and the drain electrode 175 may include at least one metal of gold (Au), copper (Cu), nickel (Ni), aluminum (Al), molybdenum (Mo), chromium (Cr), tantalum (Ta), titanium (Ti), an alloy thereof, or a combination thereof.

Referring to FIG. 1B, an organic thin film transistor according to embodiment includes a substrate 110; an organic semiconductor layer 154 formed on the substrate 110; a source electrode 173 and a drain electrode 175 electrically connected to the organic semiconductor layer 154; a gate insulating layer 140 formed on the organic semiconductor layer 154, the source electrode 173 and the drain electrode 175; and a gate electrode 124 formed on the gate insulating layer 140.

Referring to FIG. 1C, organic thin film transistor according to embodiment includes a substrate 110 intergrated with a first gate electrode 125; a first gate insulating layer 141 formed on the substrate 110; an organic semiconductor layer 154 formed on the first gate insulating layer 141; a source electrode 173 and a drain electrode 175 electrically connected to the organic semiconductor layer 154; a second gate insulating layer 140 formed on the organic semiconductor layer 154, the source electrode 173 and the drain electrode 175; and a second gate electrode 124 formed on the second gate electrode 124.

Although FIGS. 1A to 1C illustrate some embodiments of thin film transistor, inventive concepts are not limited thereto, and it may be applied to all organic thin film transistors.

The organic thin film transistor may be applied to a switch or driving device of various electronic devices, and the electronic device may include, for example, a liquid crystal display (LCD), an organic light emitting diode (OLED) display, an electrophoretic display, an organic photoelectric device, and an organic sensor, but is not limited thereto.

Hereinafter, the embodiments are illustrated in more detail with reference to examples. However, these examples are non-limiting, and inventive concepts are not limited thereto.

SYNTHESIS EXAMPLES

Synthesis Example 1

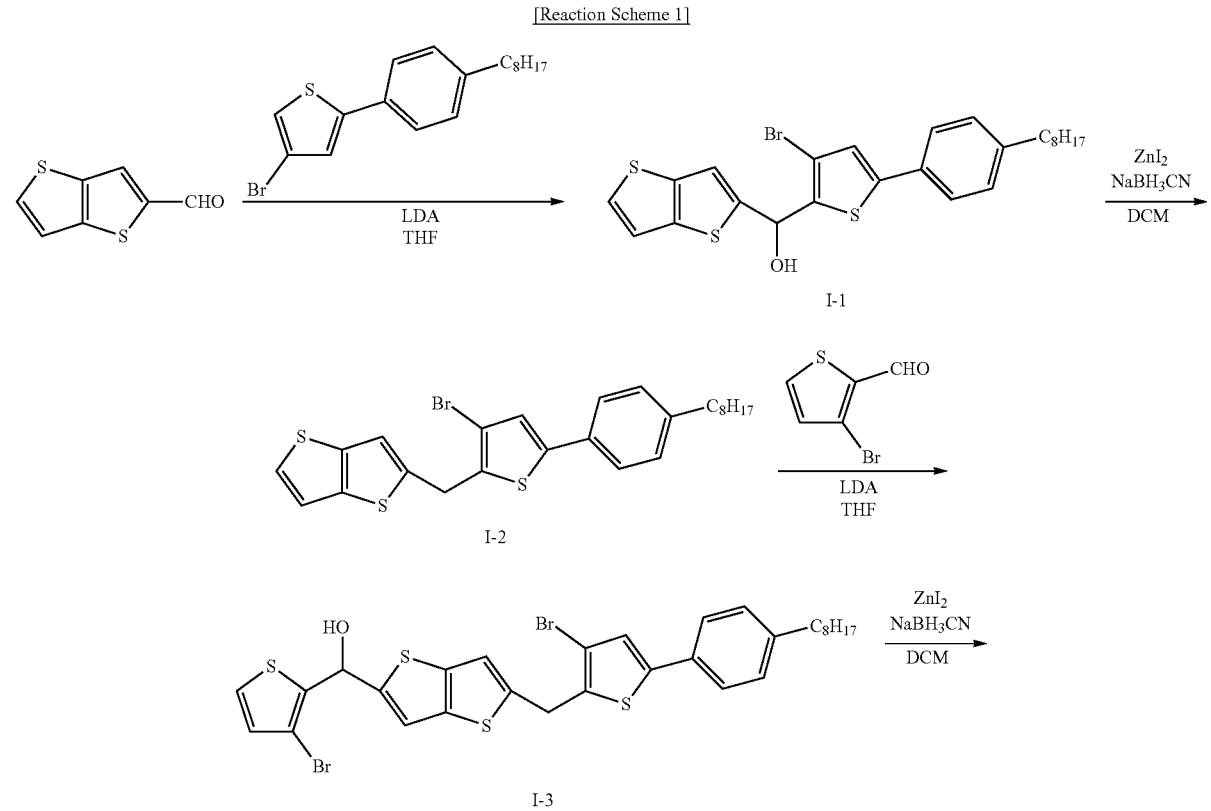

[Reaction Scheme 1]

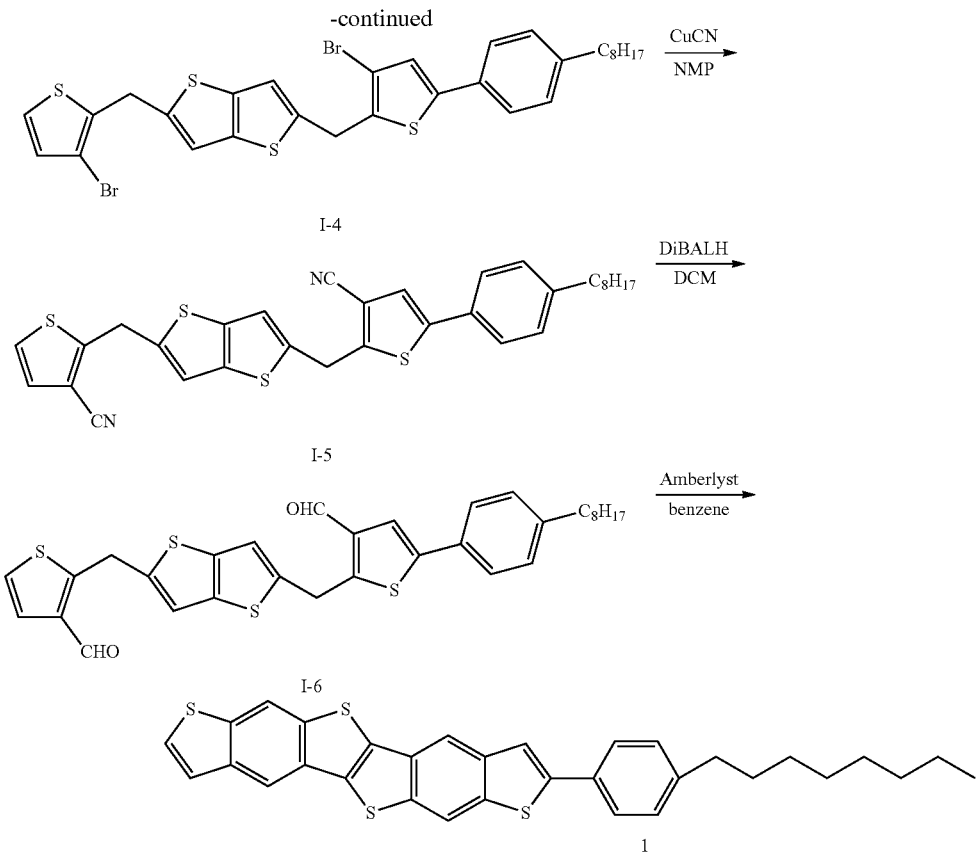

Synthesis of Intermediate I-1

4-bromo-2-(4-octylphenyl)thiophene (7.04 g, 20.0 mmol) is dissolved in dry tetrahydrofuran (THF) and then, cooled down to −78° C. lithium diisopropylamide (LDA)(a 2 M solution) (12.02 ml, 24 mmol) is slowly added thereto in a dropwise fashion, and then, thieno[3,2-b]thiophene-2-carbaldehyde (3.07 g, 20.0 mmol) is added thereto. Subsequently, the temperature is slowly increased up to room temperature, and the obtained mixture is stirred for 12 hours. 100 mL of an ammonium chloride saturated solution is added thereto, and the resultant is extracted with ethyl acetate and then, several times washed with water. Subsequently, the obtained extract is dried with magnesium sulfate, filtered, and after removing an ethylacetate solvent therefrom, purified through silica column chromatography to obtain Intermediate I-1. Herein, a yield is 89%.

Synthesis of Intermediate I-2

Intermediate I-1 (9.26 g, 17.8 mmol) is dissolved in 1 L of dichloromethane, and $ZnI_2$ (9.10 g, 28.5 mmol) and $NaCNBH_3$ (7.84 g, 124.8 mmol) are slowly added thereto. The obtained mixture is stirred at room temperature for 24 hours, and 200 mL of an ammonium chloride saturated solution is added thereto to complete a reaction. Subsequently, the resultant is extracted with dichloromethane and then, several times washed with water. Then, the obtained extract is dried with $MgSO_4$ and concentrated under a reduced pressure to obtain yellow oil. This material is purified through silica column chromatography to obtain Intermediate I-2. Herein, a yield is 89%.

Synthesis of Intermediate I-3

Intermediate I-2 (8.63 g, 17.1 mmol) is dissolved in 300 mL of dry tetrahydrofuran (THF) and then, cooled down to −78° C. LDA (a 2 M solution) (10.3 ml, 20.6 mmol) is slowly added thereto in a dropwise fashion, and 3-bromo-thiophene-2-carbaldehyde (3.6 g, 18.9 mmol) is added thereto. Subsequently, the temperature is slowly increased, and the obtained mixture is stirred at room temperature for 12 hours. Then, 100 mL of an ammonium chloride saturated solution is added thereto, and the resultant is extracted with dichloromethane and several times washed with water. Subsequently, the obtained extract is dried with magnesium sulfate and purified through silica column chromatography to obtain Intermediate I-3. Herein, a yield is 49%.

Synthesis of Intermediate I-4

Intermediate I-3 (5.2 g, 7.4 mmol) is dissolved in 1 L of dichloromethane, and then, $ZnI_2$ (3.8 g, 11.9 mmol) and $NaCNBH_3$ (3.3 g, 52.1 mmol) are slowly added thereto. The obtained mixture is stirred at room temperature for 24 hours, respectively washed with an ammonium chloride saturated solution and water, dried with $MgSO_4$, and then, concentrated under a reduced pressure to obtain yellow oil. This material is purified through silica column chromatography to obtain Intermediate I-4. Herein, a yield was 98%.

Synthesis of Intermediate I-5

Intermediate I-4 (0.3 g, 0.44 mmol) is dissolved in 6 ml of N-methylpyrrolidone, copper cyanide (CuCN) (0.16 g, 1.8 mmol) is added thereto, and the mixture is allowed to stay in a microwave reactor under 50 W at 180° C. for 2 hours. When a reaction is complete, the resultant is poured into a 1N HCl solution, and the obtained mixture is stirred for 30 minutes. Then, a solid therein is filtered and then, extracted with dichloromethane. Subsequently, the obtained extract is washed with water, dried with magnesium sulfate, and treated through a short path column by using Celite and silica to obtain Intermediate I-5. Herein, a yield is 81%.

Synthesis of Intermediate I-6

Intermediate 5 (1.6 g, 4.2 mmol) is dissolved in 200 mL of dichloromethane and then, cooled down to 0° C. Subsequently, diisobutyl aluminum hydride (DIBALH, a 1.0 M solution in cyclohexane) (10.1 ml, 10.1 mmol) is added thereto, and the obtained mixture is stirred for 4 hours. Then, the reaction solution is poured into a mixed solvent of methanol and water (methanol:water=2:1) to complete a reaction, and the resultant is extracted with dichloromethane and then, washed with water and brine. Subsequently, an organic layer therefrom is dried with $MgSO_4$, concentrated under a reduced pressure, and purified through silica chromatography to obtain Intermediate I-6. Herein, a yield is 91%.

Synthesis of Compound 1

Intermediate I-6 (1.1 g, 1.9 mmol) is dissolved in 100 mL of benzene, Amberlyst 15 (1.1 g) is added thereto, and water is removed therefrom by using a Dean-Stark trap, while the mixture is stirred and refluxed. After about 24 hours, a light yellow liquid generated therein is cooled down to room temperature to form a white precipitate. The precipitated floating materials are filtered and thus collected and then, recrystallized and purified in a mixed solution of hexane and chloroform to obtain Compound 1 as a white solid. Herein, a yield is 72%.

MS (MALDI-TOF-MS, m/z) 540.248 (M+)

Synthesis Example 2

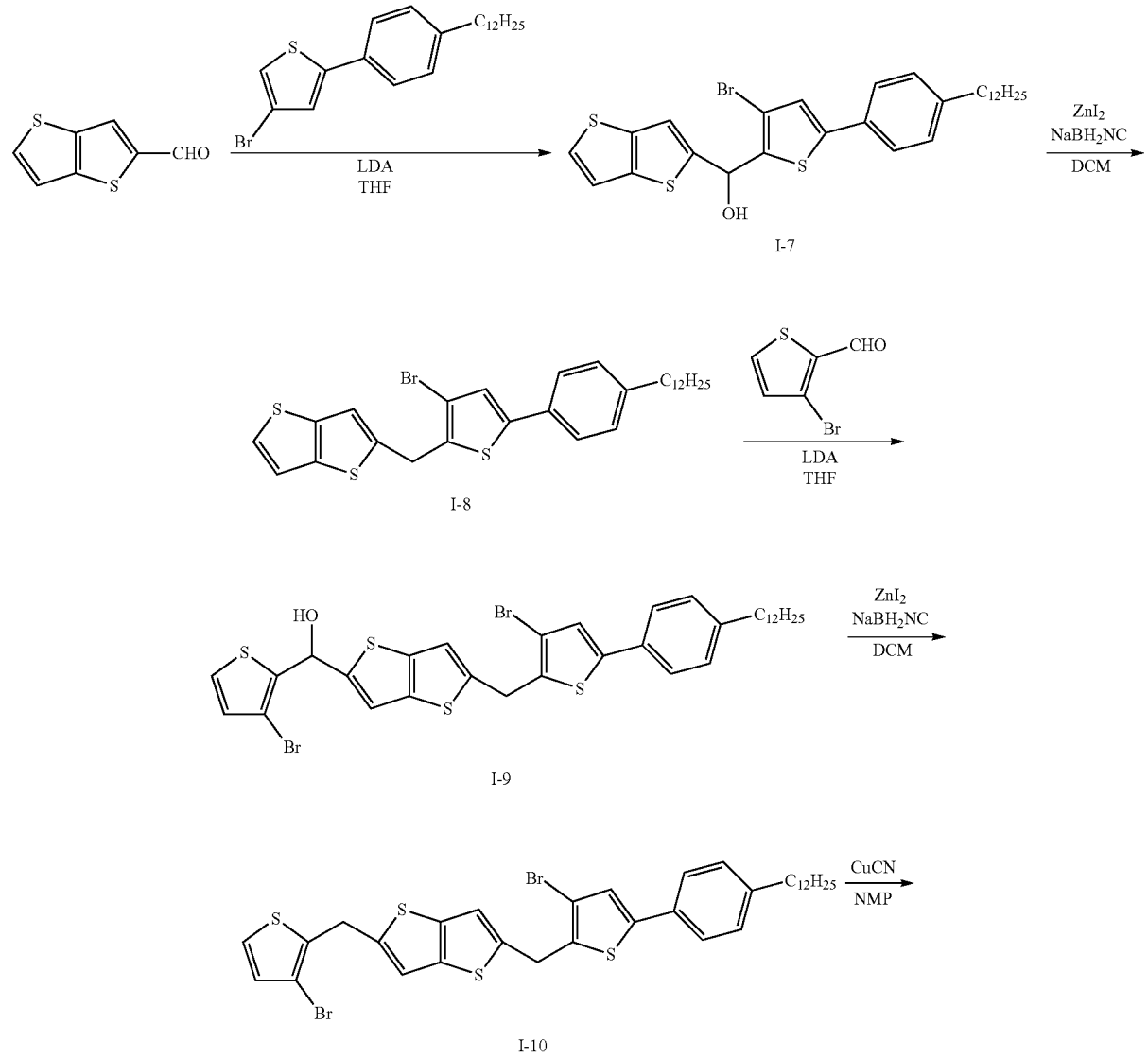

[Reaction Scheme 2]

-continued
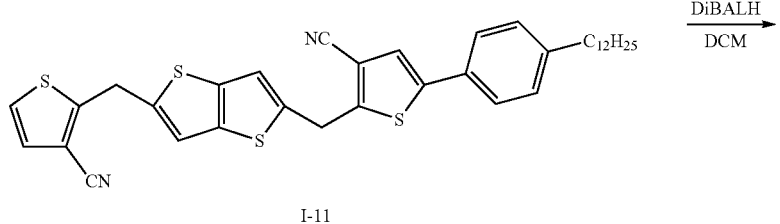
I-11
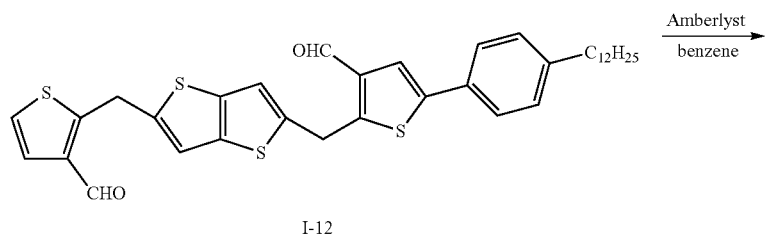
I-12
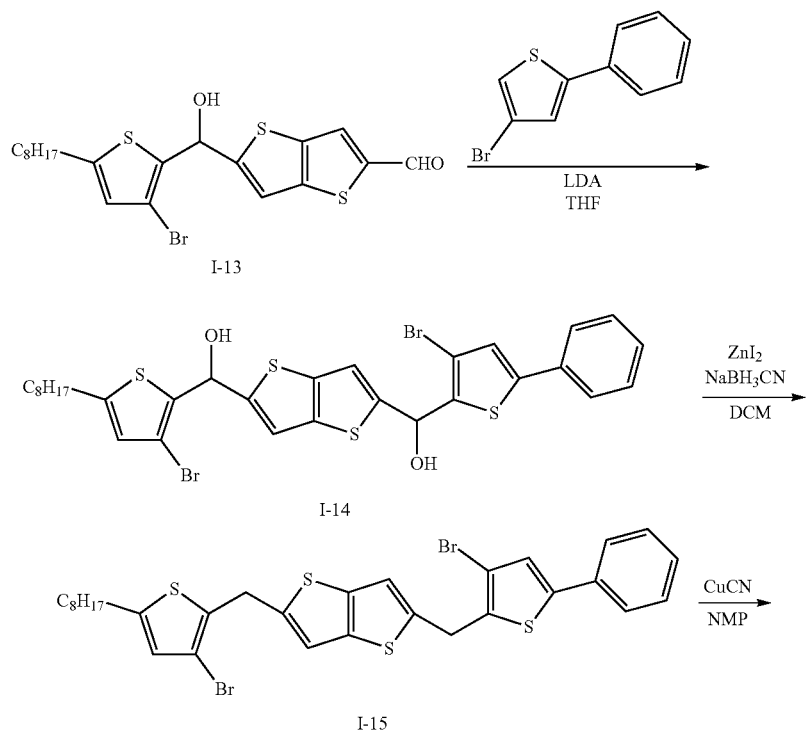
2
Compound 2 is obtained according to the same synthesis method as Synthesis Example 1 except that 4-bromo-2-(4-dodecylphenyl)thiophene is used instead of the 4-bromo-2-(4-octylphenyl)thiophene. Herein, a total yield is 20%.
MS (MALDI-TOF-MS, m/z) 596.318 (M+)
Synthesis Example 3
[Reaction Scheme 3]
I-13
I-14
I-15

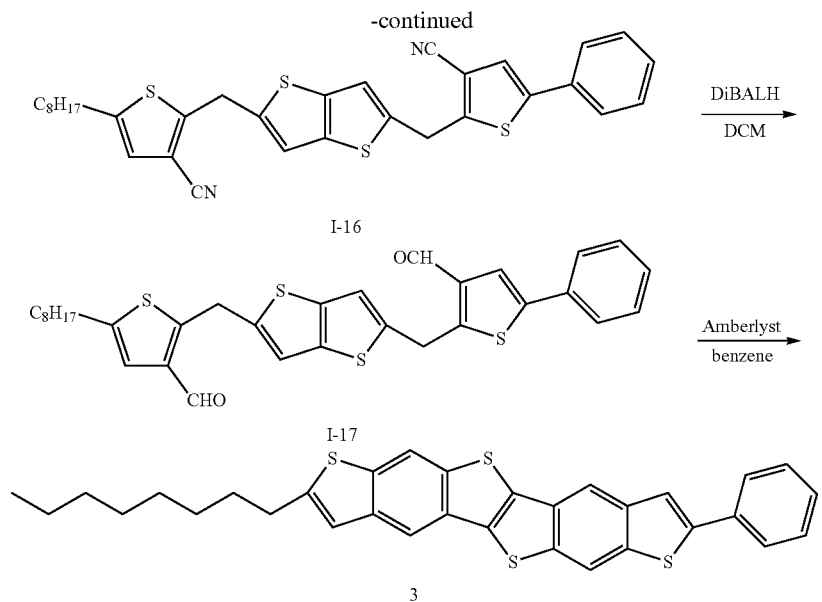

Synthesis of Intermediate I-14

4-bromo-2-phenylthiophene (6 g, 25.1 mmol) is dissolved in dry tetrahydrofuran (THF) and then, cooled down to −78° C. LDA (a 2 M solution) (15.1 ml, 30 mmol) is slowly added thereto in a dropwise fashion, and Intermediate I-13 (12.1 g, 25.1 mmol) is added thereto. Subsequently, the temperature is slowly increased, and the obtained mixture is stirred at room temperature for 12 hours. 100 mL of an ammonium chloride saturated solution is added thereto, and the resultant is extracted with ethyl acetate and then, several times washed with water. The obtained extract is dried with magnesium sulfate, filtered, and after removing the ethylacetate solvent, purified through silica column chromatography to obtain Intermediate I-14. Herein, a yield is 67%.

1H NMR (500 MHz, CDCl3): δ ppm 7.53 (d, 2H), 7.43 (m, 2H), 7.31 (d, 1H), 7.17 (s, 1H), 7.13 (s, 1H), 7.01 (s, 1H), 6.6 (s, 1H), 6.37 (d, 1H), 4.26 (s, 2H), 2.68 (t, 2H), 1.58 (m, 2H), 1.27 (m, 14H), 0.87 (t, 3H)

Synthesis of Intermediate I-15

Intermediate I-14 (10 g, 13.84 mmol) is dissolved in 700 mL of dichloromethane, and $ZnI_2$ (7.07 g, 23.5 mmol) and $NaCNBH_3$ (6.09 g, 96.86 mmol) are slowly added thereto. Subsequently, the mixture is stirred at room temperature for 24 hours, then, passed through a celite pad, respectively washed with an ammonium chloride saturated solution and water, dried with $MgSO_4$, and concentrated under a reduced pressure to obtain yellow oil. The obtained material is purified through silica column chromatography to obtain Intermediate I-15. Herein, a yield is 92%.

1H NMR (500 MHz, CDCl3): δ ppm 7.50 (d, 2H), 7.35 (m, 2H), 7.28 (m, 1H), 7.13 (s, 1H), 7.03 (s, 1H), 7.0 (s, 1H), 6.6 (s, 1H), 6.37 (d, 1H), 4.33 (s, 2H), 4.26 (s, 2H), 2.69 (t, 2H), 1.55 (m, 2H), 1.27 (m, 14H), 0.87 (t, 3H)

Synthesis of Intermediate I-16

Intermediate I-15 (9 g, 12.73 mmol) is dissolved in 135 ml of N-methylpyrrolidone, copper cyanide (CuCN) (3.42 g, 38.2 mmol) is added thereto, and the mixture is reacted in a microwave reactor under a condition of 50 W at 185° C. for 2 hours. When a reaction is complete, the resultant is poured into a 1 N HCl solution and then, stirred for 30 minutes. Subsequently, the obtained solid is filtered and then, extracted with chloroform ($CHCl_3$) and washed with water. Then, the obtained extract is dried with magnesium sulfate, filtered, and after removing the chloroform solvent, purified through silica column chromatography to obtain Intermediate I-16. Herein, a yield is 60%.

1H NMR (500 MHz, CDCl3): δ ppm 7.49 (d, 2H), 7.38 (m, 2H), 7.34 (d, 1H), 7.29 (s, 1H), 7.11 (s, 1H), 7.06 (s, 1H), 6.79 (s, 1H), 4.55 (s, 2H), 4.48 (s, 2H), 2.70 (t, 2H), 1.59 (m, 2H), 1.27 (m, 14H), 0.86 (t, 3H)

Synthesis of Intermediate I-17

Intermediate I-16 (4.56 g, 7.61 mmol) is dissolved in 600 mL of dichloromethane and then, cooled down to 0° C. Subsequently, diisobutyl aluminum hydride (DIBALH, a 1.0 M solution in cyclohexane) (18.27 ml, 18.27 mmol) is added thereto and then, stirred for 2 hours. Then, 5% citric acid is poured thereinto to complete a reaction, and the resultant is extracted with chloroform ($CHCl_3$) and washed with water and brine. Subsequently, an organic layer therefrom is dried with $MgSO_4$, concentrated under a reduced pressure and then, purified through silica chromatography to obtain Intermediate I-17. Herein, a yield is 67%.

1H NMR (500 MHz, CDCl3): δ ppm 10.1 (s, 1H), 9.99 (s, 1H), 7.59 (s, 1H), 7.55 (d, 2H), 7.37 (m, 2H), 7.31 (m, 1H), 7.06 (d, 2H), 7.01 (s, 1H), 4.76 (s, 2H), 4.69 (s, 2H), 2.71 (t, 2H), 1.62 (m, 2H), 1.28 (m, 14H), 0.87 (t, 3H)

Synthesis of Compound 3

Intermediate I-17 (3.1 g, 5.12 mmol) is dissolved in 300 mL of benzene, Amberlyst 15 (3.1 g) is added thereto, and then, water is removed therefrom by using a Dean-Stark trap, while the mixture is stirred and refluxed. After about 24 hours, a light yellow solid is precipitated. Subsequently, a temperature thereof is decreased down to room temperature, Amberlyst 15 is precipitated, and floating materials are skimmed and filtered to obtain Compound 3 as a desired yellow solid. Herein, a yield is 50%.
MS (MALDI-TOF-MS, m/z) 540.174 (M+)
Synthesis Example 4
Compound 4 is obtained according to the same synthesis method as Synthesis Example 3 except that Intermediate I-18 is used instead of Intermediate I-13. Herein, a total yield is 15%.
MS (MALDI-TOF-MS, m/z) 596.421 (M+)
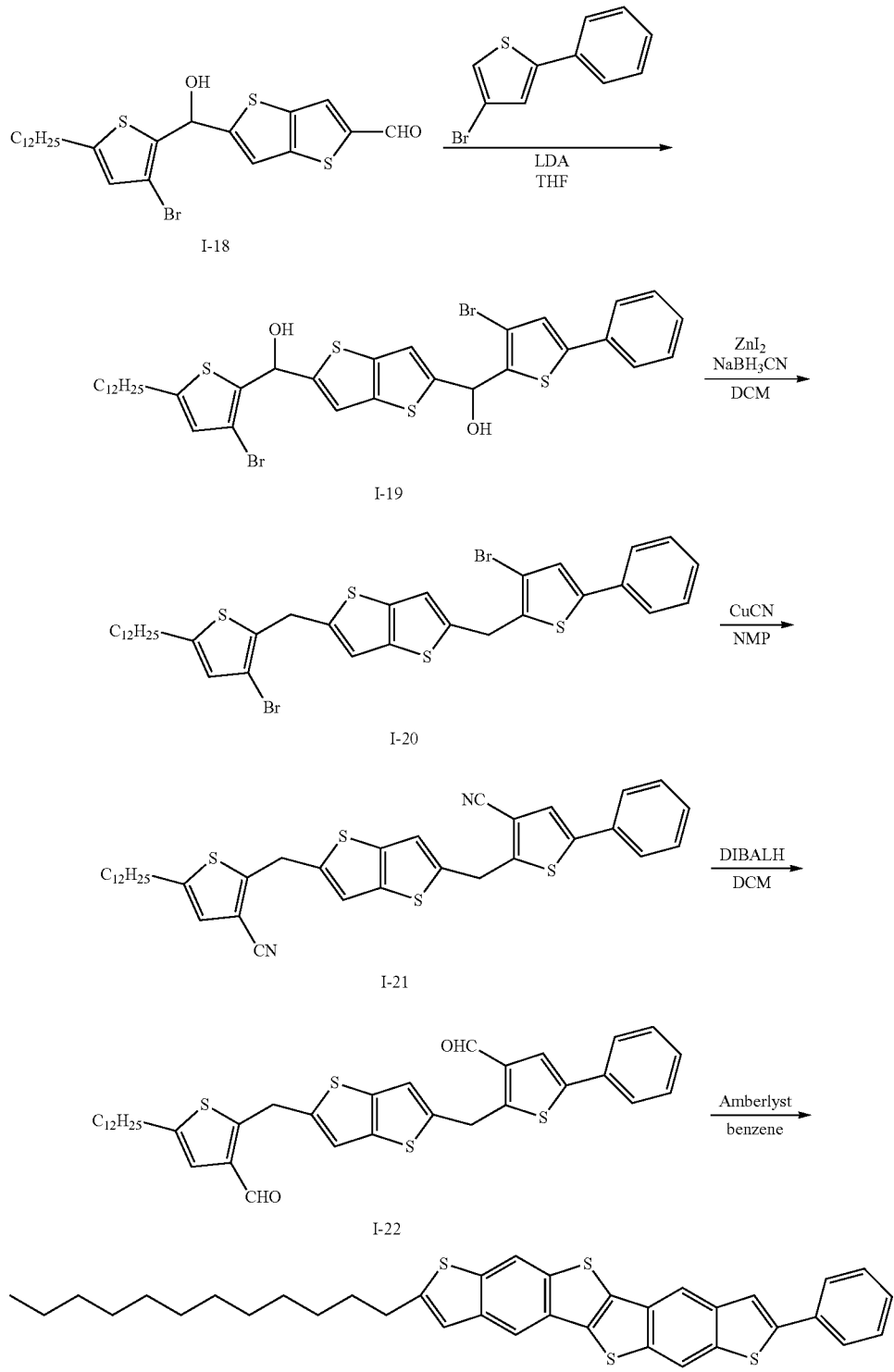

Manufacture of Organic Thin Film

Preparation Example 1

First, a washed silicon wafer substrate coated with $SiO_2$ to be 3000 Å thick is exposed to $O_2$ plasma and then, dipped in an octadecyl trichlorosilane solution diluted in hexane at a concentration of 4 mM to change the surface to be hydrophobic. Subsequently, a crucible including the compound of Synthesis Example 1 and a crucible including the compound of Synthesis Example 2 are respectively heated and then, codeposited to form a 600 Å-thick organic thin film by opening a main shutter at 135° C. Herein, the compound of Synthesis Example 1 and the compound of Synthesis Example 2 are codeposited in a ratio of deposition rates of 1:1 and accordingly, the organic thin film includes the compound of Synthesis Example 1 and the compound of Synthesis Example 2 in a weight ratio of about 1:1.

Comparative Preparation Example 1

An organic thin film is formed according to the same method as Preparation Example 1 except that the compound of Synthesis Example 1 alone is deposited instead of the compound of Synthesis Example 1 and the compound of Synthesis Example 2.

Comparative Preparation Example 2

An organic thin film is formed according to the same method as Preparation Example 1 except that the compound of Synthesis Example 2 alone is deposited instead of the compound of Synthesis Example 1 and the compound of Synthesis Example 2.

Preparation Example 2

The compound of Synthesis Example 1 and the compound of Synthesis Example 2 at each concentration of 0.05 wt % are dissolved in o-dichlorobenzene.

The solution is dropped between the silicon wafer substrate covered with 3000 Å-thick $SiO_2$ and a glass substrate disposed on the silicon wafer substrate to form an organic thin film on the silicon wafer substrate in a gap-cast method (regarding the gap-cast method, refer to an article "ADVANCED MATERIALS" 2011, 23, P. 1626 to 1629). Subsequently, the organic thin film is annealed for 4 hours on a hot plate at 120° C. in a nitrogen globe box. Herein, the compound of Synthesis Example 1 and the compound of Synthesis Example 2 are included in a weight ratio of about 1:1 in the solution, and accordingly, the organic thin film includes the compound of Synthesis Example 1 and the compound of Synthesis Example 2 in a weight ratio of about 1:1.

Comparative Preparation Example 3

An organic thin film is formed according to the same method as Preparation Example 2 except that the compound of Synthesis Example 1 alone is used instead of the compound of Synthesis Example 1 and the compound of Synthesis Example 2.

Comparative Preparation Example 4

An organic thin film is formed according to the same method as Preparation Example 2 except that the compound of Synthesis Example 2 alone is used instead of the compound of Synthesis Example 1 and the compound of Synthesis Example 2.

Preparation Example 3

First, a washed silicon wafer substrate coated with $SiO_2$ to be 3000 Å thick is exposed to $O_2$ plasma and then, dipped in an octadecyl trichlorosilane solution diluted in hexane to a concentration of 4 mM to change the surface to be hydrophobic. Subsequently, the compound of in Synthesis Example 3 and the compound of Synthesis Example 4 are separately put in each different crucible and respectively heated and then, codeposited to form a 600 Å-thick organic thin film by opening an main shutter at 170° C. Herein, the compound of Synthesis Example 3 and the compound of Synthesis Example 4 are deposited in a ratio of deposition rates of about 1:3, and accordingly, the organic thin film includes the compound of Synthesis Example 3 and the compound of Synthesis Example 4 in a weight ratio of about 1:3. Subsequently, the organic thin film is annealed for 2 hours on a hot plate at 210° C. in a nitrogen globe box.

Comparative Preparation Example 5

An organic thin film is formed according to the same method as Preparation Example 3 except that the compound of Synthesis Example 3 alone is used instead of the compound of Synthesis Example 3 and the compound of Synthesis Example 4.

Comparative Preparation Example 6

An organic thin film is formed according to the same method as Preparation Example 3 except that the compound of Synthesis Example 4 alone is used instead of the compound of Synthesis Example 3 and the compound of Synthesis Example 4.

Evaluation I

Crack generation degrees of the organic thin films of Preparation Examples and Comparative Preparation Examples are evaluated.

The crack generation degrees are evaluated by examining the surfaces of the organic thin films of Preparation Examples and Comparative Preparation Examples with an optical microscope (MX51, OLYMPUS Corp.)

Figure 2:
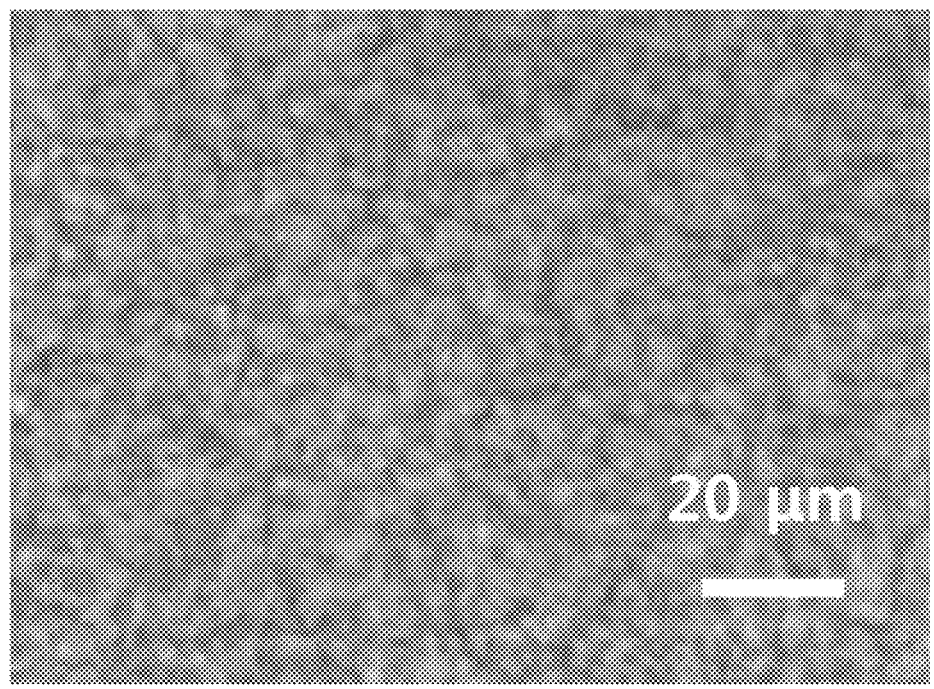
FIG. 2 is an optical photograph of an organic thin film according to Preparation Example 1.
Figure 3:
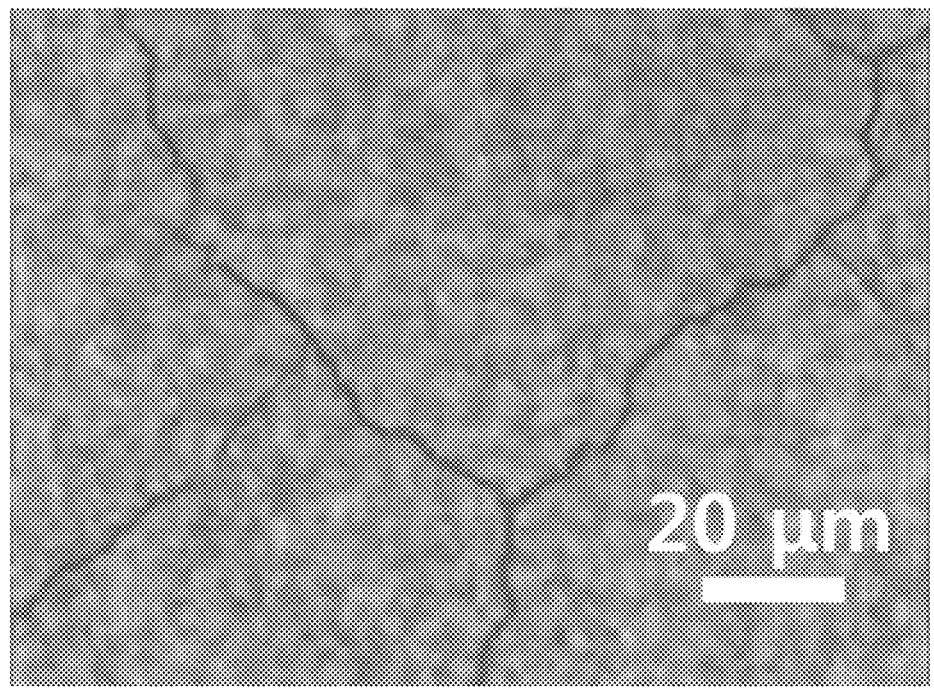
FIG. 3 is an optical photograph of an organic thin film according to Comparative Preparation Example 1.
Figure 4:
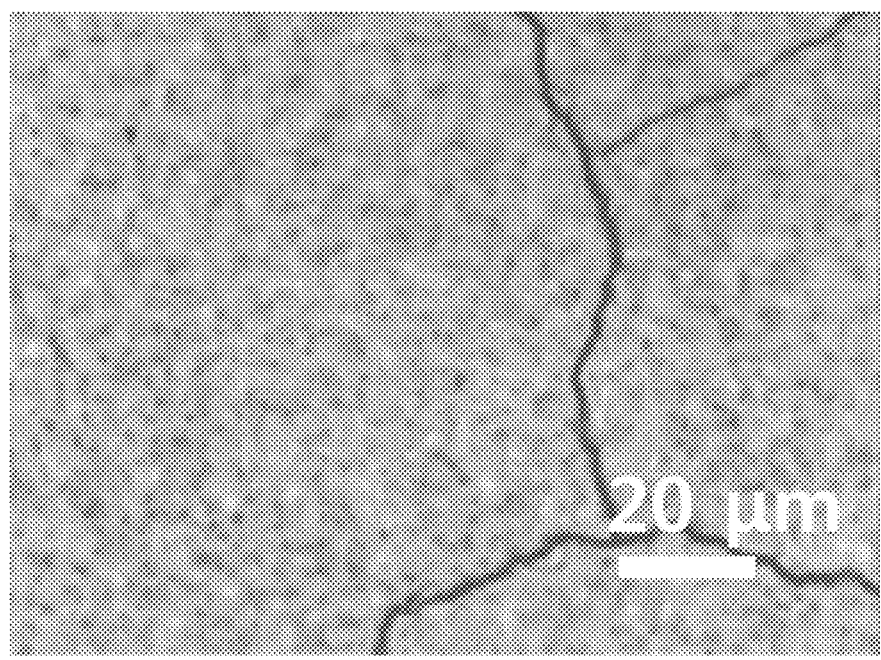
FIG. 4 is an optical photograph of an organic thin film according to Comparative Preparation Example 2.

FIG. 2 is an optical photograph of an organic thin film according to Preparation Example 1, FIG. 3 is an optical photograph of an organic thin film according to Comparative Preparation Example 1, and FIG. 4 is an optical photograph of an organic thin film according to Comparative Preparation Example 2.

Referring to FIGS. 2 to 4, in the organic thin film of Preparation Example 1, a crack is not almost observed, but in the organic thin films of Comparative Preparation Examples 1 and 2, a plurality of cracks are observed.

Figure 5:
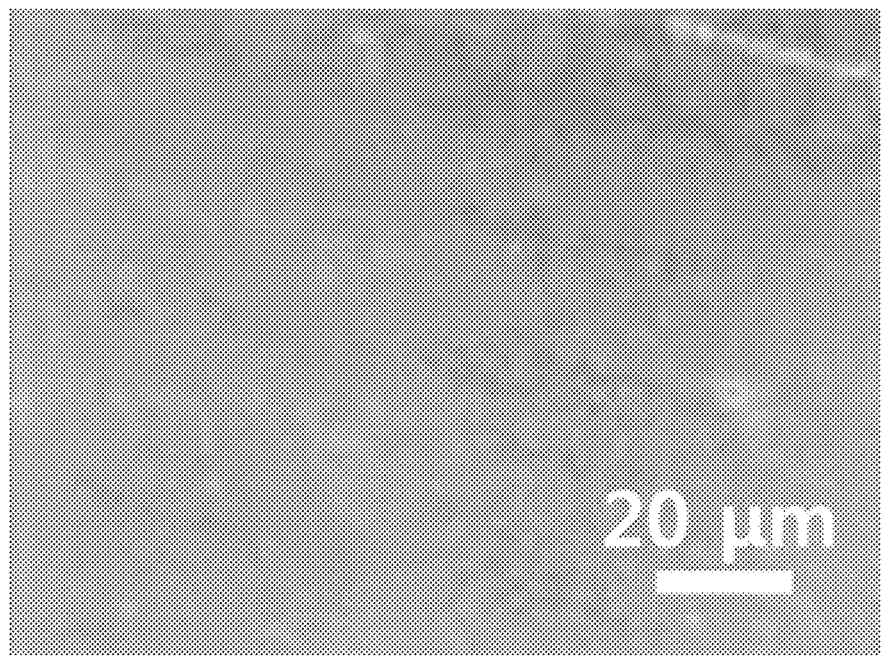
FIG. 5 is an optical photograph of an organic thin film according to Preparation Example 2.
Figure 6:
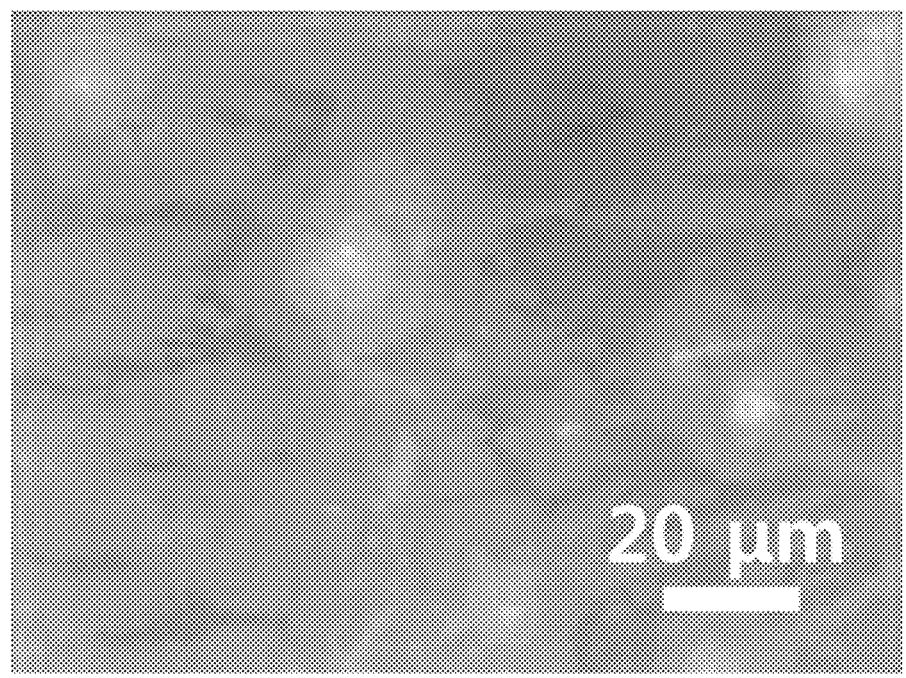
FIG. 6 is an optical photograph of an organic thin film according to Comparative Preparation Example 3.
Figure 7:
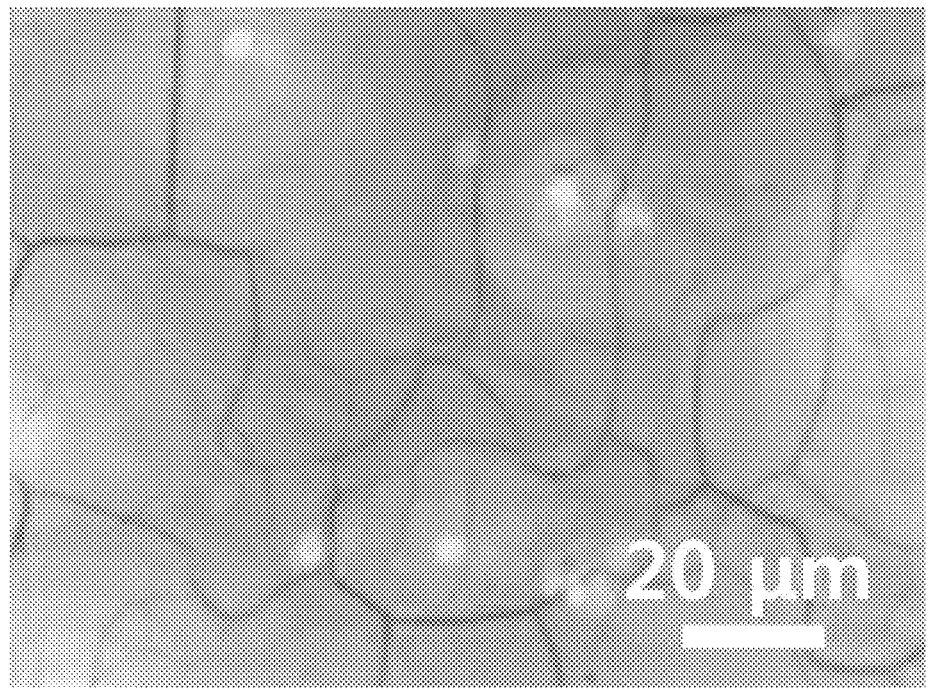
FIG. 7 is an optical photograph of an organic thin film according to Comparative Preparation Example 4.

FIG. 5 is an optical photograph of an organic thin film according to Preparation Example 2, FIG. 6 is an optical photograph of an organic thin film according to Comparative Preparation Example 3, and FIG. 7 is an optical photograph of an organic thin film according to Comparative Preparation Example 4.

Referring to FIGS. 5 to 7, in the organic thin film of Preparation Example 2, a crack is not almost observed, but in the organic thin films of Comparative Preparation Examples 3 and 4, a plurality of cracks are observed.

Figure 8:
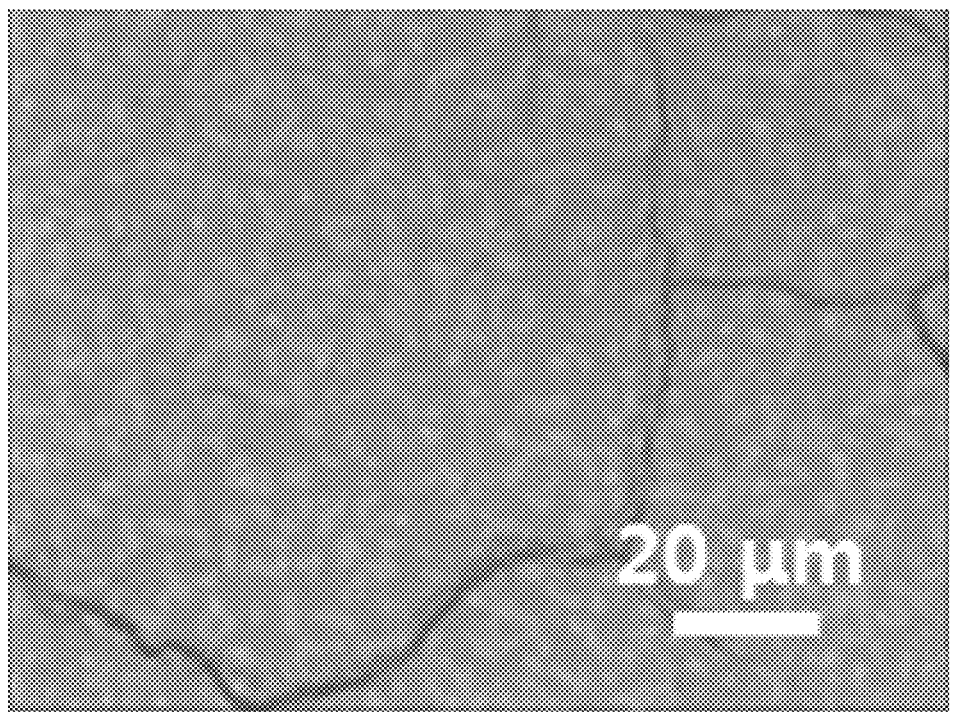
FIG. 8 is an optical photograph of an organic thin film according to Preparation Example 3.
Figure 9:
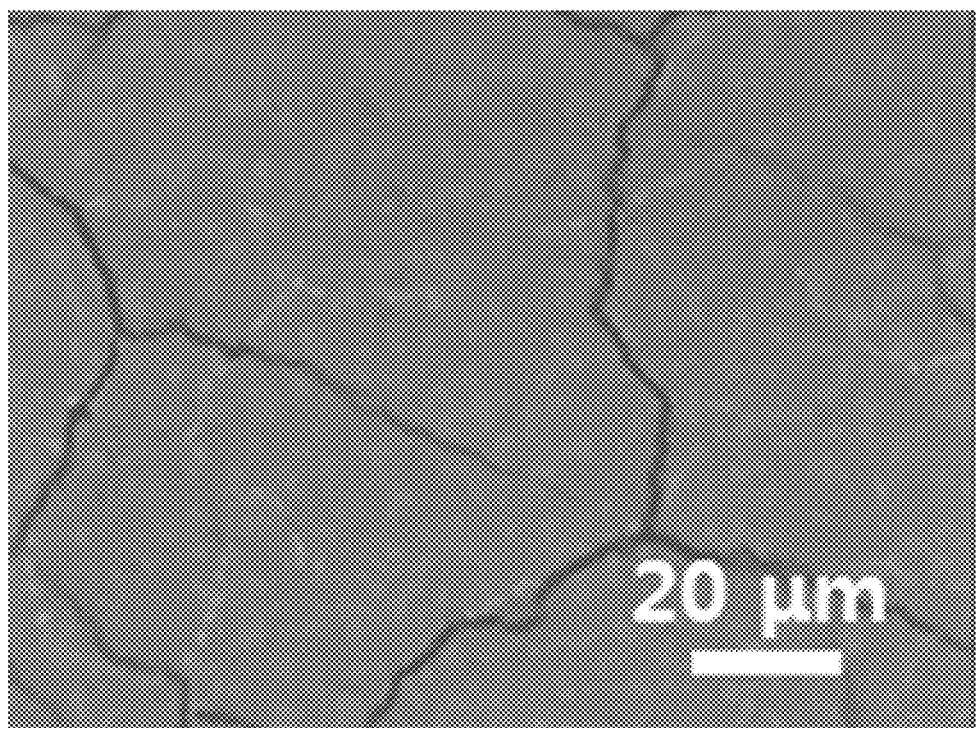
FIG. 9 is an optical photograph of an organic thin film according to Comparative Preparation Example 5.
Figure 10:
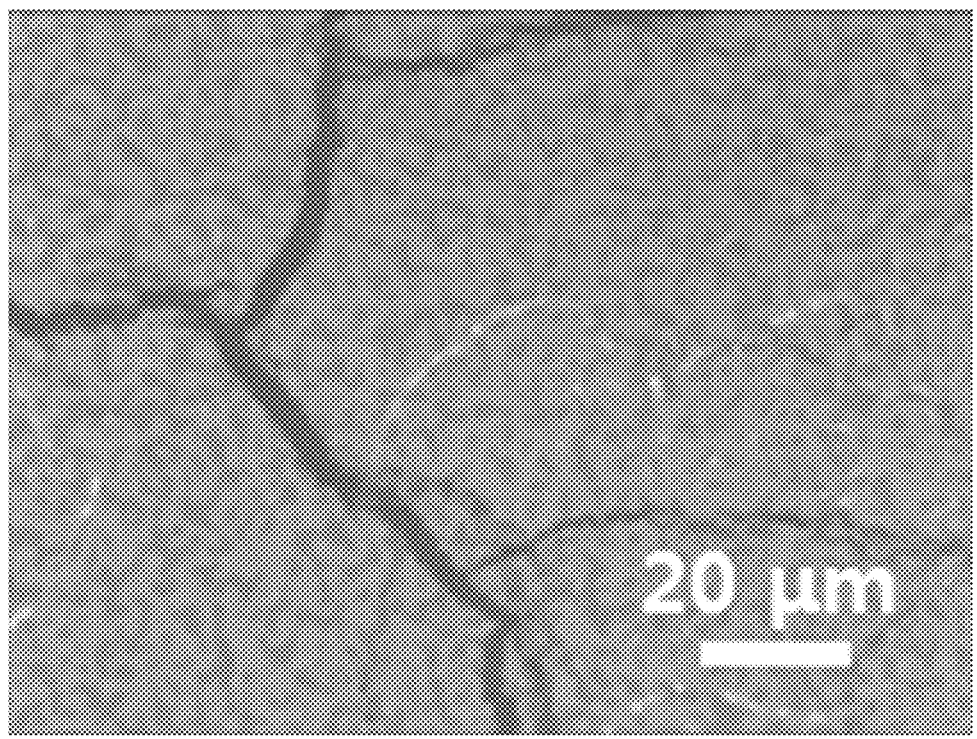
FIG. 10 is an optical photograph of an organic thin film according to Comparative Preparation Example 6.

FIG. 8 is an optical photograph of an organic thin film according to Preparation Example 3, FIG. 9 is an optical photograph of an organic thin film according to Comparative Preparation Example 5, and FIG. 10 is an optical photograph of an organic thin film according to Comparative Preparation Example 6.

Referring to FIGS. 8 to 10, the organic thin film of Preparation Example 3 shows a greatly crack decrease compared with the organic thin films according to Comparative Preparation Examples 5 and 6.

Manufacture of Organic Thin Film Transistor

Example 1

First, a washed silicon wafer substrate coated with $SiO_2$ to be 3000 Å thick is exposed to $O_2$ plasma and then, dipped in an octadecyl trichlorosilane solution diluted in hexane to a concentration of 4 mM to change the surface to be hydrophobic. Subsequently, the compound of Synthesis Example 1 and the compound of Synthesis Example 2 are codeposited to be 500 Å thick at 135° C. in a vacuum vapor deposition method to form an organic semiconductor layer. Then, the organic semiconductor layer is annealed for 4 hours at 120° C. on a hot plate in a nitrogen globe box. Herein, the compound of Synthesis Example 1 and the compound of Synthesis Example 2 are respectively deposited at a deposition rate of 0.10 Å/s, and accordingly, the organic semiconductor layer includes the compound of Synthesis Example 1 and the compound of Synthesis Example 2 in a weight ratio of 1:1. Subsequently, on the organic semiconductor layer, source and drain electrodes are disposed by depositing gold (Au) to be 1000 Å thick by using a shadow mask.

Comparative Example 1

An organic thin film transistor is manufactured according to the same method as Example 1 except that the compound of Synthesis Example 1 alone is deposited instead of the compound of Synthesis Example 1 and the compound of Synthesis Example 2 to manufacture an organic thin film transistor.

Comparative Example 2

An organic thin film transistor is manufactured according to the same method as Example 1 except that the compound of Synthesis Example 2 alone is deposited instead of the compound of Synthesis Example 1 and the compound of Synthesis Example 2 to manufacture an organic thin film transistor.

Example 2

The compound of Synthesis Example 1 and the compound of Synthesis Example 2 at each concentration of 0.05 wt % are dissolved in o-dichlorobenzene to prepare a solution.

First, the solution is dropped between a silicon wafer substrate cleaned and covered with 3000 Å $SiO_2$ and a glass substrate disposed on the silicon wafer substrate to form an about 300 Å-thick organic semiconductor layer in a gap cast method (regarding the gap-cast method, refer to an article "ADVANCED MATERIALS" 2011, 23, P. 1626 to 1629). Subsequently, the organic semiconductor layer is annealed for 4 hours on a hot plate at 120° C. in a nitrogen globe box. Herein, the solution includes the compound of Synthesis Example 1 and the compound of Synthesis Example 2 in a weight ratio of about 1:1, and accordingly, the organic semiconductor layer includes the compound of Synthesis Example 1 and the compound of Synthesis Example 2 in a weight ratio of about 1:1. Subsequently, on the organic semiconductor layer, source and drain electrodes are disposed by depositing gold (Au) to be 1000 Å thick by using a shadow mask to manufacture an organic thin film transistor.

Comparative Example 3

An organic thin film transistor is manufactured according to the same method as Example 2 except that a solution including the compound of Synthesis Example 1 alone is used instead of the mixed solution including the compound of Synthesis Example 1 and the compound of Synthesis Example 2.

Comparative Example 4

An organic thin film transistor is manufactured according to the same method as Example 2 except that a solution including the compound of Synthesis Example 2 alone is used instead of the mixed solution including the compound of Synthesis Example 1 and the compound of Synthesis Example 2.

Example 3

First, a washed silicon wafer substrate coated with $SiO_2$ to be 3000 Å thick is exposed to $O_2$ plasma and then, dipped in an octadecyl trichlorosilane solution diluted in hexane to a concentration of 4 mM to change the surface to be hydrophobic. Subsequently, an organic semiconductor layer is formed by codepositing the compound of Synthesis Example 3 and the compound of Synthesis Example 4 to be 500 Å thick on the substrate at 170° C. in a vacuum vapor deposition method. Herein, the compound of Synthesis Example 3 and the compound of Synthesis Example 4 are codeposited at each deposition rate of 0.05 Å/s and 0.15 Å/s (in a ratio of deposition rates=1:3), and accordingly, the organic semiconductor layer includes the compound of Synthesis Example 3 and the compound of Synthesis Example 4 in a weight ratio of about 1:3. Subsequently, the organic semiconductor layer is annealed for 2 hours on a hot plate at 210° C. in a nitrogen globe box. On the organic semiconductor layer, source and drain electrodes are disposed by depositing gold (Au) to be 1000 Å thick by using a shadow mask to manufacture an organic thin film transistor.

Comparative Example 5

An organic thin film transistor is manufactured according to the same method as Example 3 except that the compound of Synthesis Example 3 alone is used instead of the compound of Synthesis Example 3 and the compound of Synthesis Example 4.

Comparative Example 6

An organic thin film transistor is manufactured according to the same method as Example 3 except that the compound of Synthesis Example 4 alone is used instead of the compound of Synthesis Example 3 and the compound of Synthesis Example 4.

Evaluation II

Electrical characteristics of the thin film transistors according to Examples and Comparative Examples are calculated.

The charge mobility of the thin film transistors is obtained by obtaining a graph having $(I_{SD})^{1/2}$ and $V_G$ as variables from a saturation region current equation and a slope in the graph.

$$I_{SD} = \frac{WC_0}{2L}\mu(V_G - V_T)^2$$

$$\sqrt{I_{SD}} = \sqrt{\frac{\mu C_0 W}{2L}}(V_G - V_T)$$

$$\text{slope} = \sqrt{\frac{\mu C_0 W}{2L}}$$

$$\mu_{FET} = (\text{slope})^2 \frac{2L}{C_0 W}$$

In the equations, $I_{SD}$ is a source-drain current, $\mu$ or $\mu_{FET}$ is charge mobility, $C_0$ is electrostatic capacity of a gate insulating layer, W is a channel width, L is a channel length, $V_G$ is a gate voltage, and $V_T$ is a threshold voltage.

The results are shown in Tables 1 to 3.

TABLE 1

|  | Charge mobility (cm²/Vs) | Threshold voltage ($V_T$, V) | S.S |
|---|---|---|---|
| Example 1 | 7.90 ± 0.31 | −2.04 ± 0.25 | 0.99 ± 0.10 |
| Comparative Example 1 | 5.07 ± 0.73 | 14.82 ± 2.19 | 1.88 ± 0.62 |
| Comparative Example 2 | 3.49 ± 0.55 | 2.33 ± 0.64 | 2.51 ± 0.43 |

TABLE 2

|  | Charge mobility (cm²/Vs) | Threshold voltage ($V_T$, V) | S.S |
|---|---|---|---|
| Example 2 | 1.44 ± 0.36 | 5.26 ± 1.07 | 1.81 ± 0.57 |
| Comparative Example 3 | 0.54 ± 0.47 | 1.44 ± 2.93 | 1.68 ± 0.20 |
| Comparative Example 4 | 0.50 ± 0.19 | 7.30 ± 4.07 | 4.41 ± 4.79 |

TABLE 3

|  | Charge mobility (cm²/Vs) |
|---|---|
| Example 3 | 7.41 ± 0.91 |
| Comparative Example 5 | 3.87 ± 0.23 |
| Comparative Example 6 | 6.70 ± 0.35 |

* S.S: Subthreshold Swing. The variation values of the gate voltage required to reduce a current by 10 times at a current of a threshold voltage ($V_T$). The smaller the values, the better the performance of the thin film transistors because they can be turned on/off with a small gate voltage.

Referring to Tables 1 to 3, it may be confirmed that the organic thin film transistors according to Examples have improved electrical characteristics compared with the organic thin film transistors according to Comparative Examples.

While this disclosure has been described in connection with what is presently considered to be practical example embodiments, it is to be understood that inventive concepts are not limited to the disclosed embodiments. On the contrary, inventive concepts are intended to cover various modifications and equivalent arrangements included within the spirit and scope of the appended claims.

What is claimed is:

1. An organic thin film, comprising:
   a first compound represented by one of Chemical Formula 1A and 1B, and
   a second compound that is different from the first compound, the second compound represented by one of Chemical Formulae 2A and 2B:

[Chemical Formula 1A]

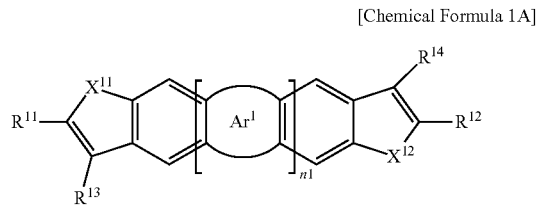

[Chemical Formula 1B]

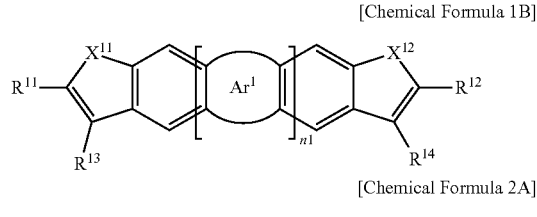

[Chemical Formula 2A]

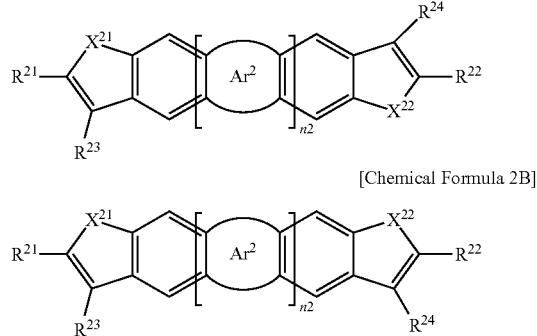

[Chemical Formula 2B]

wherein, in Chemical Formulae 1A, 1B, 2A, and 2B,
$X^{11}$, $X^{12}$, $X^{21}$, and $X^{22}$ are independently one of O, S, Se, Te, and $NR^a$,
$R^{11}$ and $R^{12}$ are different from each other or $R^{13}$ and $R^{14}$ are different from each other,
$R^{21}$ and $R^{22}$ are different from each other or $R^{23}$ and $R^{24}$ are different from each other,
$R^{11}$ to $R^{14}$, $R^{21}$ to $R^{24}$, and $R^a$ are independently hydrogen, a substituted or unsubstituted C1 to C30 alkyl group, a substituted or unsubstituted C2 to C30 alkenyl group, a substituted or unsubstituted C2 to C30 alkynyl group, a substituted or unsubstituted C3 to C30 cycloalkyl group, a substituted or unsubstituted C3 to C30 cycloalkenyl group, a substituted or unsubstituted C1 to C30 alkoxy group, a substituted or unsubstituted C3 to C30 heterocycloalkyl group, a substituted or unsubstituted C3 to C30 heterocycloalkenyl group, a substituted or unsubstituted C6 to C30 aryl group, a substituted or unsubstituted C7 to C30 alkylaryl group, a substituted or unsubstituted C6 to C30 aryloxy group, a substituted or unsubstituted C3 to C30 heteroaryl group, a substituted or unsubstituted C4 to C30 alkylheteroaryl group, a halogen, a cyano group, or a combination thereof, n1 and n2 are 1, and $Ar^1$ and $Ar^2$ independently include a structure represented by a substituted or unsubstituted group listed in Group 1,

[Group 1]

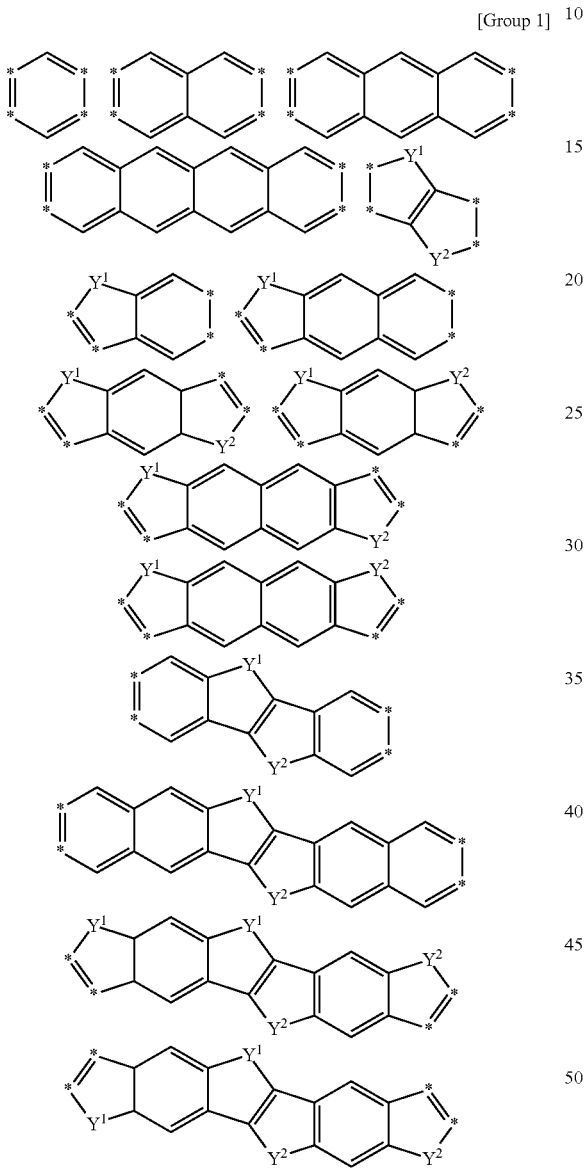

wherein, in Group 1, $Y^1$ and $Y^2$ are independently one of O, S, Se, and Te, and

* is a linking point.

2. The organic thin film of claim 1, wherein the organic thin film includes a mixture of the first compound and the second compound.

3. The organic thin film of claim 1, wherein $Ar^1$ and $Ar^2$ independently comprise at least one of a substituted or unsubstituted furan ring, a substituted or unsubstituted thiophene ring, a substituted or unsubstituted selenophene ring, and substituted or unsubstituted tellurophene ring.

4. The organic thin film of claim 1, wherein $Ar^1$ and $Ar^2$ are the same.

5. The organic thin film of claim 4, wherein $X^{11}$ and $X^{21}$ are the same, and $X^{12}$ and $X^{22}$ are the same.

6. The organic thin film of claim 1, wherein $R^{11}$ and $R^{21}$ are hydrogen, and $R^{12}$ and $R^{22}$ are different from each other and are independently a substituted or unsubstituted C1 to C30 alkyl group, a substituted or unsubstituted C2 to C30 alkenyl group, a substituted or unsubstituted C2 to C30 alkynyl group, a substituted or unsubstituted C3 to C30 cycloalkyl group, a substituted or unsubstituted C3 to C30 cycloalkenyl group, a substituted or unsubstituted C1 to C30 alkoxy group, a substituted or unsubstituted C3 to C30 heterocycloalkyl group, a substituted or unsubstituted C3 to C30 heterocycloalkenyl group, a substituted or unsubstituted C6 to C30 aryl group, a substituted or unsubstituted C7 to C30 alkylaryl group, a substituted or unsubstituted C6 to C30 aryloxy group, a substituted or unsubstituted C3 to C30 heteroaryl group, a substituted or unsubstituted C4 to C30 alkylheteroaryl group, a halogen, a cyano group, or a combination thereof.

7. The organic thin film of claim 1, wherein $R^{11}$ and $R^{21}$ are independently a substituted or unsubstituted C1 to C30 linear alkyl group, a substituted or unsubstituted C2 to C30 linear alkenyl group, a substituted or unsubstituted C2 to C30 linear alkynyl group, a substituted or unsubstituted C1 to C30 alkoxy group, or a combination thereof, $R^{12}$ and $R^{22}$ are independently a substituted or unsubstituted C3 to C30 branched alkyl group, a substituted or unsubstituted C3 to C30 branched alkenyl group, a substituted or unsubstituted C3 to C30 branched alkynyl group, or a combination thereof, and $R^{11}$ and $R^{21}$ are different from each other or $R^{12}$ and $R^{22}$ are different from each other.

8. The organic thin film of claim 1, wherein $R^{11}$ and $R^{21}$ are independently a substituted or unsubstituted C1 to C30 alkyl group, a substituted or unsubstituted C2 to C30 alkenyl group, a substituted or unsubstituted C2 to C30 alkynyl group, a substituted or unsubstituted C1 to C30 alkoxy group, or a combination thereof, $R^{12}$ and $R^{22}$ are independently a substituted or unsubstituted C3 to C30 cycloalkyl group, a substituted or unsubstituted C3 to C30 cycloalkenyl group, a substituted or unsubstituted C3 to C30 heterocycloalkyl group, a substituted or unsubstituted C3 to C30 heterocycloalkenyl group, a substituted or unsubstituted C6 to C30 aryl group, a substituted or unsubstituted C7 to C30 alkylaryl group, a substituted or unsubstituted C6 to C30 aryloxy group, a substituted or unsubstituted C3 to C30 heteroaryl group, a substituted or unsubstituted C4 to C30 alkylheteroaryl group, or a combination thereof, and $R^{11}$ and $R^{21}$ are different from each other or $R^{12}$ and $R^{22}$ are different from each other.

9. The organic thin film of claim 1, wherein $R^{11}$ and $R^{21}$ are independently a substituted or unsubstituted C3 to C30 cycloalkyl group, a substituted or unsubstituted C3 to C30 cycloalkenyl group, a substituted or unsubstituted C6 to C30 aryl group, or a combination thereof, $R^{12}$ and $R^{22}$ are independently a substituted or unsubstituted C3 to C30 heterocycloalkyl group, a substior unsubstituted C3 to C30 heterocycloalkenyl group, a substituted or unsubstituted C3 to C30 heteroaryl group, a substituted or unsubstituted C4 to C30 alkylheteroaryl group, or a combination thereof, and $R^{11}$ and $R^{21}$ are different from each other or $R^{12}$ and $R^{22}$ are different from each other.

10. The organic thin film of claim 1, wherein $R^{12}$ and $R^{22}$ are different from each other and are independently one of a substituted or unsubstituted C1 to C30 alkyl group, a substituted or unsubstituted C7 to C30 alkylaryl group, and a substituted or unsubstituted C4 to C30 alkylheteroaryl group.

11. The organic thin film of claim 10, wherein $R^{22}$ includes an alkyl group having a longer chain than $R^{12}$.

12. The organic thin film of claim 10, wherein $R^{11}$ and $R^{21}$ are independently one of hydrogen, a substituted or unsubstituted C6 to C30 aryl group, and a substituted or unsubstituted C3 to C30 heteroaryl group.

13. The organic thin film of claim 1, wherein the first compound and the second compound are included in a weight ratio of about 10:90 to about 90:10.

14. The organic thin film of claim 1, further comprising:
a third compound,
wherein the third compound is a substituted or unsubstituted fused polycyclic heteroaromatic compound that is different from the first compound and the second compound.

15. An electronic device comprising:
the organic thin film of claim 1.

16. An organic thin film transistor, comprising
a gate electrode;
a source electrode and a drain electrode; and
an organic semiconductor layer overlapping with the gate electrode, the source electrode and the drain electrode electrically connected to the organic semiconductor layer,
the organic semiconductor layer including a first compound and a second compound different from the first compound, the first compound represented by one of Chemical Formula 1A and 1B, and
the second compound being represented by one of Chemical Formulae 2A and 2B,

[Chemical Formula 1A]

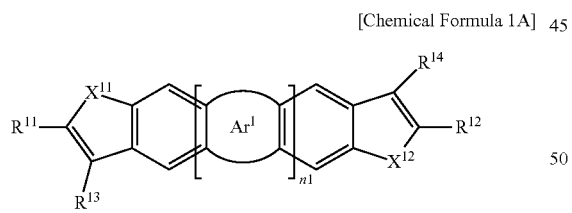

[Chemical Formula 1B]

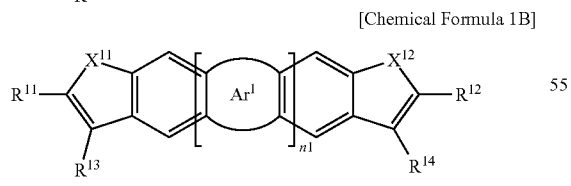

[Chemical Formula 2A]

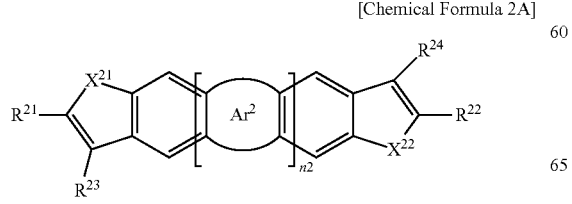

-continued

[Chemical Formula 2B]

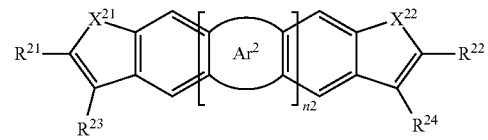

wherein, in Chemical Formulae 1A, 1B, 2A, and 2B, $X^{11}$, $X^{12}$, $X^{21}$, and $X^{22}$ are independently one of O, S, Se, Te, and $NR^a$, $R^{11}$ and $R^{12}$ are different from each other or $R^{13}$ and $R^{14}$ are different from each other, $R^{21}$ and $R^{22}$ are different from each other or $R^{23}$ and $R^{24}$ are different from each other, $R^{11}$ to $R^{14}$, $R^{21}$ to $R^{24}$, and $R^a$ are independently hydrogen, a substituted or unsubstituted C1 to C30 alkyl group, a substituted or unsubstituted C2 to C30 alkenyl group, a substituted or unsubstituted C2 to C30 alkynyl group, a substituted or unsubstituted C3 to C30 cycloalkyl group, a substituted or unsubstituted C3 to C30 cycloalkenyl group, a substituted or unsubstituted C1 to C30 alkoxy group, a substituted or unsubstituted C3 to C30 heterocycloalkyl group, a substituted or unsubstituted C3 to C30 heterocycloalkenyl group, a substituted or unsubstituted C6 to C30 aryl group, a substituted or unsubstituted C7 to C30 alkylaryl group, a substituted or unsubstituted C6 to C30 aryloxy group, a substituted or unsubstituted C3 to C30 heteroaryl group, a substituted or unsubstituted C4 to C30 alkylheteroaryl group, a halogen, a cyano group, or a combination thereof, n1 and n2 are 1, and $Ar^1$ and $Ar^2$ are independently include a structure represented by a substituted or unsubstituted group listed in Group 1,

[Group 1]

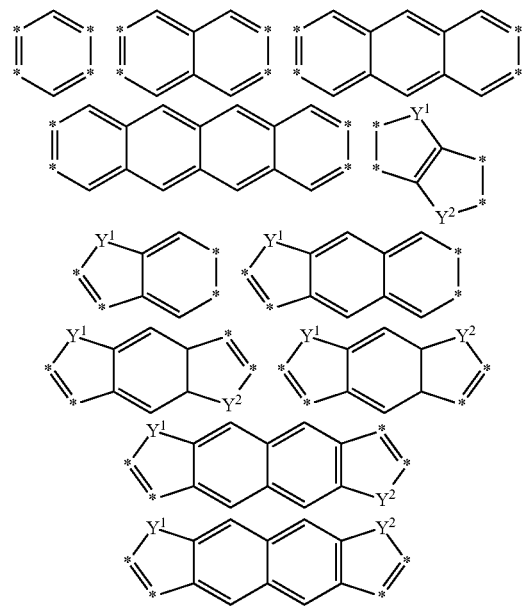

-continued

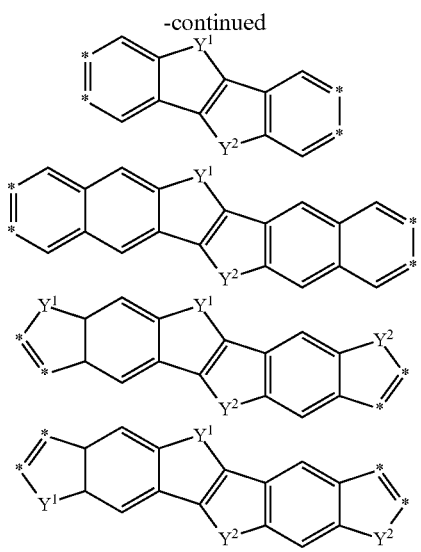

wherein, in Group 1,
$Y^1$ and $Y^2$ are independently one of O, S, Se, and Te, and
* is a linking point.

17. The organic thin film transistor of claim 16, wherein the organic semiconductor layer includes a mixture of the first compound and the second compound.

18. The organic thin film transistor of claim 16, wherein $Ar^1$ and $Ar^2$ independently comprise at least one of a substituted or unsubstituted furan ring, a substituted or unsubstituted thiophene ring, a substituted or unsubstituted selenophene ring, and substituted or unsubstituted tellurophene ring.

19. The organic thin film transistor of claim 16, wherein $Ar^1$ and $Ar^2$ are the same.

20. The organic thin film transistor of claim 19, wherein
$X^{11}$ and $X^{21}$ are the same, and
$X^{12}$ and $X^{22}$ are the same.

21. The organic thin film transistor of claim 16, wherein
$R^{11}$ and $R^{21}$ are hydrogen, and
$R^{12}$ and $R^{22}$ are different from each other and are independently a substituted or unsubstituted C1 to C30 alkyl group, a substituted or unsubstituted C2 to C30 alkenyl group, a substituted or unsubstituted C2 to C30 alkynyl group, a substituted or unsubstituted C3 to C30 cycloalkyl group, a substituted or unsubstituted C3 to C30 cycloalkenyl group, a substituted or unsubstituted C1 to C30 alkoxy group, a substituted or unsubstituted C3 to C30 heterocycloalkyl group, a substituted or unsubstituted C3 to C30 heterocycloalkenyl group, a substituted or unsubstituted C6 to C30 aryl group, a substituted or unsubstituted C7 to C30 alkylaryl group, a substituted or unsubstituted C6 to C30 aryloxy group, a substituted or unsubstituted C3 to C30 heteroaryl group, a substituted or unsubstituted C4 to C30 alkylheteroaryl group, a halogen, a cyano group, or a combination thereof.

22. The organic thin film transistor of claim 16, wherein $R^{11}$ and $R^{21}$ are independently a substituted or unsubstituted C1 to C30 linear alkyl group, a substituted or unsubstituted C2 to C30 linear alkenyl group, a substituted or unsubstituted C2 to C30 linear alkynyl group, a substituted or unsubstituted C1 to C30 alkoxy group, or a combination thereof, $R^{12}$ and $R^{22}$ are independently a substituted or unsubstituted C3 to C30 branched alkyl group, a substituted or unsubstituted C3 to C30 branched alkenyl group, a substituted or unsubstituted C3 to C30 branched alkynyl group, or a combination thereof, and
$R^{11}$ and $R^{21}$ are different from each other or $R^{12}$ and $R^{22}$ are different from each other.

23. The organic thin film transistor of claim 16, wherein $R^{11}$ and $R^{21}$ are independently a substituted or unsubstituted C1 to C30 alkyl group, a substituted or unsubstituted C2 to C30 alkenyl group, a substituted or unsubstituted C2 to C30 alkynyl group, a substituted or unsubstituted C1 to C30 alkoxy group, or a combination thereof,
$R^{12}$ and $R^{22}$ are independently a substituted or unsubstituted C3 to C30 cycloalkyl group, a substituted or unsubstituted C3 to C30 cycloalkenyl group, a substituted or unsubstituted C3 to C30 heterocycloalkyl group, a substituted or unsubstituted C3 to C30 heterocycloalkenyl group, a substituted or unsubstituted C6 to C30 aryl group, a substituted or unsubstituted C7 to C30 alkylaryl group, a substituted or unsubstituted C6 to C30 aryloxy group, a substituted or unsubstituted C3 to C30 heteroaryl group, a substituted or unsubstituted C4 to C30 alkylheteroaryl group, or a combination thereof, and
$R^{11}$ and $R^{21}$ are different from each other or $R^{12}$ and $R^{22}$ are different from each other.

24. The organic thin film transistor of claim 16, wherein $R^{11}$ and $R^{21}$ are independently a substituted or unsubstituted C3 to C30 cycloalkyl group, a substituted or unsubstituted C3 to C30 cycloalkenyl group, a substituted or unsubstituted C6 to C30 aryl group, or a combination thereof,
$R^{12}$ and $R^{22}$ are independently a substituted or unsubstituted C3 to C30 heterocycloalkyl group, a substituted or unsubstituted C3 to C30 heterocycloalkenyl group, a substituted or unsubstituted C3 to C30 heteroaryl group, a substituted or unsubstituted C4 to C30 alkylheteroaryl group, or a combination thereof, and
$R^{11}$ and $R^{21}$ are different from each other or $R^{12}$ and $R^{22}$ are different from each other.

25. The organic thin film transistor of claim 16, wherein $R^{12}$ and $R^{22}$ are different from each other and are independently one of a substituted or unsubstituted C1 to C30 alkyl group, a substituted or unsubstituted C7 to C30 alkylaryl group, and a substituted or unsubstituted C4 to C30 alkylheteroaryl group.

26. The organic thin film transistor of claim 25, wherein $R^{22}$ include an alkyl group having a longer chain than $R^{12}$.

27. The organic thin film transistor of claim 25, wherein $R^{11}$ and $R^{21}$ are the same or different and are independently one of hydrogen, a substituted or unsubstituted C6 to C30 aryl group, and a substituted or unsubstituted C3 to C30 heteroaryl group.

28. The organic thin film transistor of claim 16, wherein the first compound and the second compound are included in a weight ratio of about 10:90 to about 90:10.

29. The organic thin film transistor of claim 16, wherein the organic semiconductor layer further includes a third compound, and
the third compound is a substituted or unsubstituted fused polycyclic heteroaromatic compound that is different from the first compound and the second compound.

30. An electronic device comprising:
the organic thin film transistor of claim 16.

* * * * *